United States Patent
Cameron et al.

(10) Patent No.: US 9,913,889 B2
(45) Date of Patent: Mar. 13, 2018

(54) IMMUNOGENIC TP0751 FRAGMENTS

(71) Applicant: UVic Industry Partnerships Inc., Victoria (CA)

(72) Inventors: Caroline E. Cameron, Victoria (CA); Rebecca M. Hof, Victoria (CA); Simon A. Houston, Victoria (CA); Martin John Boulanger, Victoria (CA)

(73) Assignee: UVic Industry Partnerships Inc., Victoria (CA)

( * ) Notice: Subject to any disclaimer, the term of this patent is extended or adjusted under 35 U.S.C. 154(b) by 0 days.

(21) Appl. No.: 14/993,961

(22) Filed: Jan. 12, 2016

(65) Prior Publication Data

US 2016/0129100 A1  May 12, 2016

Related U.S. Application Data

(63) Continuation-in-part of application No. PCT/IB2014/062951, filed on Jul. 8, 2014.

(60) Provisional application No. 61/845,747, filed on Jul. 12, 2013.

(51) Int. Cl.
| | |
|---|---|
| A61K 39/02 | (2006.01) |
| C07K 14/20 | (2006.01) |
| A61K 38/00 | (2006.01) |
| A61K 39/00 | (2006.01) |

(52) U.S. Cl.
CPC .......... *A61K 39/0225* (2013.01); *C07K 14/20* (2013.01); *A61K 38/00* (2013.01); *A61K 2039/57* (2013.01); *A61K 2039/575* (2013.01)

(58) Field of Classification Search
None
See application file for complete search history.

(56) References Cited

FOREIGN PATENT DOCUMENTS

WO   WO 2006/138324 A2   12/2006

OTHER PUBLICATIONS

Cullen et al. Expert Rev. Vaccines 5(1), 67-80 (2006).*
TP_0751 Uniprot Accession O83732 Jun. 2001.*
Cameron, "Identification of a *Treponema pallidum* Laminin-Binding Protein," *Infect Immun.* 71:2525-2533, 2003.
Cameron et al., "Defining the Interaction of the *Treponema pallidum* Adhesin Tp0751 with Laminin," *Infect Immun.* 73:7485-7494, 2005.
Cameron, "Insight into dissemination of the Syphilis Spirochete, *Treponema pallidum*," University of Washington school of Public Health presentation—Mar. 7, 2013.
Cameron, "Syphilis Vaccine Development: is there Hope?," WHO Global Action Plan and Road Map for STI Vaccine meeting—Apr. 25, 2013.
Houston et al., "Bifunctional Role of the *Treponema pallidum* Extracellular Matrix Binding Adhesin Tp0751," *Infect Immun.* 79:1386-1398, 2011.
Houston et al., "Activation and Proteolytic Activity of the *Treponema pallidum* Metalloprotease, Pallilysin," *PLoS Pathog.* 8:e1002822, 2012.
Houston et al., "Understanding Spread of the Syphilis Spirochete Within the Host; Is there hope for a syphilis vaccine?," STI & AIDS World Congress 2013—Jul. 16, 2013.
Van Voorhis et al., "Serodiagnosis of Syphilis: Antibodies to Recombinant Tp0453, Tp92, and Gpd Proteins are Sensitive and Specific Indicators of Infection by *Treponema pallidum*," *J Clin Microbiol.* 41:3668-3674, 2003.
Canadian Intellectual Property Office, Written Opinion and International Search Report dated Nov. 6, 2014 for PCT/IB2014/062951.
Lithgow et al., "A defined syphilis vaccine candidate inhibits dissemination of *Treponema pallidum* subspecies *pallidum*," *Nature Comm.* 8:14273, 2017.

* cited by examiner

*Primary Examiner* — Oluwatosin A Ogunbiyi
(74) *Attorney, Agent, or Firm* — Klarquist Sparkman, LLP

(57) ABSTRACT

The present application provides methods of stimulating an immune response, such as a protective immune response against *Treponema pallidum* infection. Such methods utilize fragments of the Tp0751 protein (such as any of SEQ ID NOs: 3-10, those N-terminally truncated from amino acids 1 through 77, 1 through 114, or anywhere in between, e.g., those that start at any amino acid from 78 to 115). In some examples, a Tp0751 protein fragment has a mutated HEXXH site (HEXXH is the wild-type sequence). Also provided are the isolated soluble Tp0751 protein fragments that include a wild-type or mutated HEXXH site, as well as nucleic acids encoding such proteins and kits that include such proteins.

18 Claims, 10 Drawing Sheets

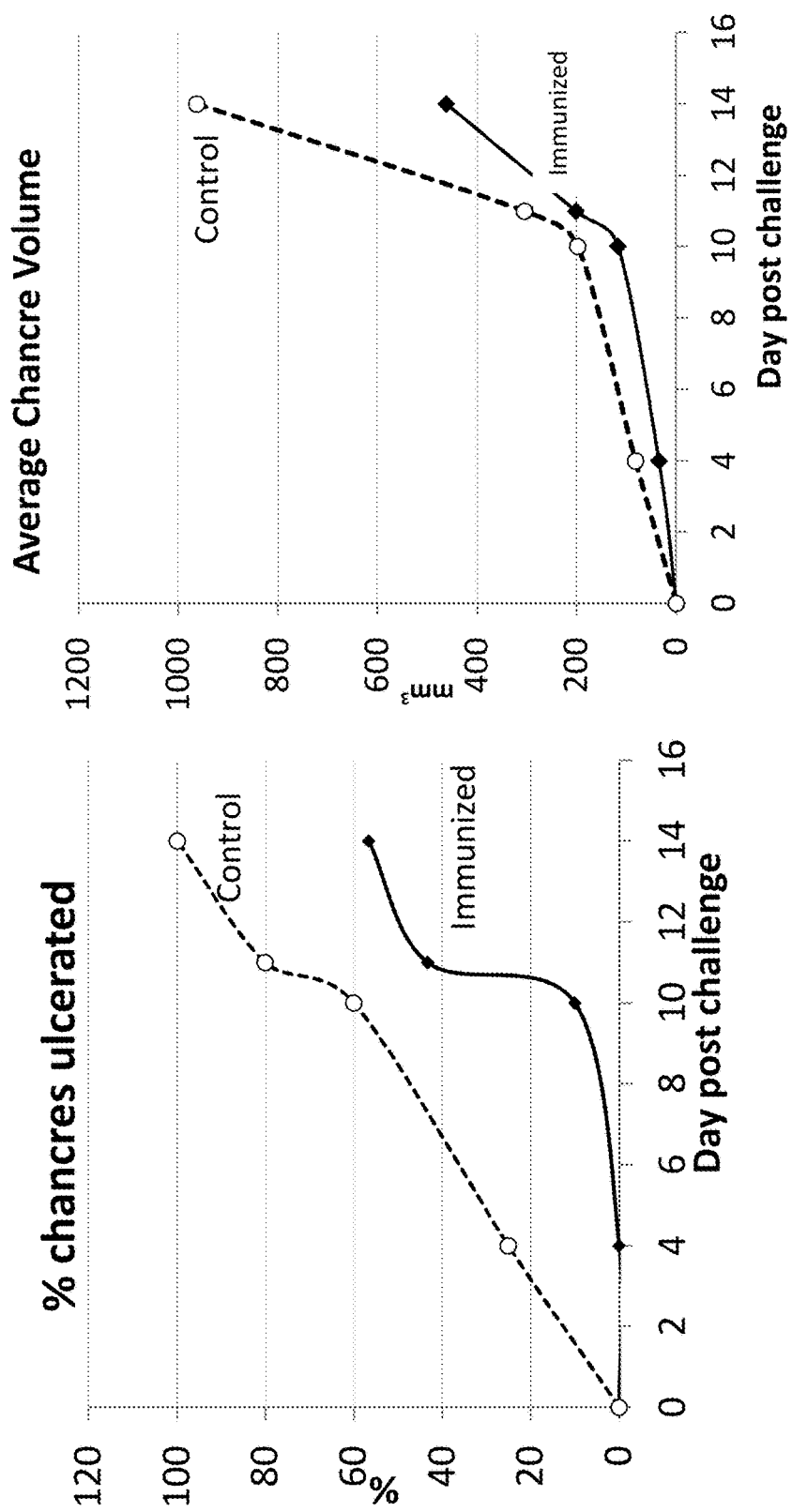

|  | SCR1 | SCR3 |
|---|---|---|
| Tp0751 | LAG.LWIQ | ..YTRYH |
| Nitrophorin | FNGDVWYV | ..LNRNK |
| Triabin | FNG.TWYL | ..FERTK |
| MPI | LSG.QWVL | ..LKKKA |
| hNGAL | FQG.KWYV | ..YGRTK |
| *Motif* | *H-\*.P\*--* | *H-\*--* |

FIG. 6C p4 GGAAQTHTQPPVQTAMRIALWNRA p6 QGALQHLLAGLWIQTEISPNSGDI p10 RKTVSFLTRNTAISSIRRRLEVTF (...NRTRTARF...)

p11 SIRRRLEVTFESHEVIHVRAVEDV

IMMUNOGENIC TP0751 FRAGMENTS

CROSS-REFERENCE TO RELATED APPLICATIONS

This application is a continuation in part of PCT/IB2014/062951 filed Jul. 8, 2014, which claims priority to U.S. Provisional Application No. 61/845,747 filed on Jul. 12, 2013, all herein incorporated by reference.

ACKNOWLEDGMENT OF GOVERNMENT SUPPORT

This invention was made with government support under AI051334 awarded by the National Institute of Allergy and Infectious Diseases. The government has certain rights in the invention.

FIELD

The application relates to fragments of the Tp0751 protein (also known as pallilysin) and methods of their use to stimulate an immune response, for example use as a vaccine in a mammal. In some examples, such stimulation of the immune response protects the mammal from subsequent *Treponema pallidum* subsp. *pallidum* infection. Also provided are Tp0751 protein fragments, nucleic acids encoding such fragments, as well as compositions including such.

BACKGROUND

Syphilis is a chronic infection caused by the spirochete *Treponema pallidum* subsp. *pallidum* that is generally transmitted either through sexual contact or vertically from an infected mother to her fetus. Syphilis is a global health concern with an estimated burden of 25 million people worldwide and an estimated annual new incidence rate of 12 million cases. Further, infection with *T. pallidum* has been shown to increase the likelihood of contracting HIV. Congenital syphilis is recognized as the most significant disease affecting pregnancies and newborns worldwide, with over 2 million pregnant women estimated to be infected with syphilis every year. Without treatment, there are adverse outcomes in 69% of cases, including spontaneous abortion or stillbirth, neonatal complications, and infant mortality.

As a multi-stage disease, syphilis has historically been called the great imitator due to the similarity of its symptoms to other diseases. Primary syphilis is characterized by a painless open sore called a chancre, which develops on average 3 weeks after infection at the site of inoculation. The chancre spontaneously resolves, and 1-3 months later secondary symptoms may present. Secondary infection typically manifests as a generalized rash, often localizing to the trunk of the body, palms of the hands, and soles of the feet. After 1-3 months, secondary symptoms resolve and the disease enters an asymptomatic latent phase. In some instances the disease can progress from latency to a tertiary stage, which can involve the development of gummas, central nervous system complications or cardiovascular disease. Since the symptoms of syphilis infection are so similar to other diseases, and resolve on their own, syphilis has always been a challenging disease to diagnose clinically.

During primary infection when a chancre is present, dark-field microscopy and/or PCR can be performed to identify spirochetes present at the site of infection. The chancre normally resolves in 4-6 weeks, and often goes unnoticed if internally located in either the anus or vagina, making diagnosis by dark-field microscopy extremely limited.

Currently, there is no vaccine available to provide protection from *T. pallidum*. Thus, there is a need for therapies that can prevent or reduce the undesirable consequences of *T. pallidum* infection.

SUMMARY

It is shown herein that 2/3 rabbits vaccinated with a fragment of Tp0751 (amino acids 24-237) and then challenged with *T. pallidum* had complete prevention of dissemination to the popliteal lymph nodes. 100% of the unvaccinated rabbits had unequivocal bacterial dissemination to the popliteal lymph nodes as demonstrated by the gold standard rabbit infectivity test. In addition, chancres from immunized animals were smaller, less ulcerated, and had fewer bacteria than control animals. Although the rabbits still had an inflammatory reaction to *T. pallidum*, the antibodies to Tp0751 generated following immunization were found to protect against certain types of damage (e.g., ulceration, necrosis). It is also shown herein that Tp0751 has a lipocalin fold, and this fold can induce platelet clot formation. In addition, it is shown herein that Tp0751 includes regions that bind to ECM components and cells.

Thus provided herein are methods of simulating an immune response in a subject, such as a mammal, by administering to the subject one or more native or non-native fragments of Tp0751. Examples of such fragments of Tp0751 include a Tp0751 protein fragment that starts at any amino acid from 78 to 115 of SEQ ID NO: 2 and ends at amino acid 237 of SEQ ID NO: 2, any of SEQ ID NOS: 3-10), or one or more Tp0751 peptide fragments that are not naturally occurring, such as a Tp0751 peptide fragment that has been modified. Examples of modifications that can be made to a Tp0751 peptide fragment (such as to any Tp0751 protein fragment that starts at any amino acid from 78 to 115 of SEQ ID NO: 2 and ends at amino acid 237 of SEQ ID NO: 2 or any of SEQ ID NOS: 3-10), include, mutations (e.g., a Tp0751 which includes a mutated HEXXH (SEQ ID NO: 45) site, such as mutating the $1^{st}$ H, E, and/or $2^{nd}$ H of this site), modification with polyethylene glycol or methoxy polyethylene glycol (PEGylation, such as for example to increase the half-life of the protein) and direct or indirect (e.g., via a linker) fusion to another peptide (such as diphtheria toxin, tetanus toxin, keyhole limpet hemocyanin (KLH), a purification tag (such as a histidine tag, e.g., 6-His). In some examples, the immune response is a B cell response. Methods for inducing serum antibodies which have neutralizing activity for *T. pallidum* are provided, for example which include administering to the subject one or more fragments of Tp0751 (such as SEQ ID NO: 3, 4, 5, 6, 7, 8, 9, 10, 15, 16, 18, 19, or 21) or a modified Tp0751 peptide. Methods for vaccinating a human against *T. pallidum* infection are provided, for example which include administering to the subject one or more fragments of Tp0751 or a modified Tp0751 peptide fragment.

Such methods can be used to prevent, treat or reduce the severity of infections caused by *T. pallidum*. In some examples, such administration protects the subject from subsequent infection by *T. pallidum*, such as a reduction in one or more consequences of *T. pallidum* infection, such as reducing one or more of chancre volume, % of chancers that ulcerate, dissemination of *T. pallidum* to lymph nodes, and the like. Such a reduction does not require 100% reduction, for example, reductions of at least 10%, at least 20%, at least 25%, at least 50%, at least 75%, at least 80%, or at least 90% can be sufficient.

Also provided are Tp0751 protein fragments (e.g., SEQ ID NO: 3, 7, 15, 16, 18, 19, or 21, which can include an N- or C-terminal tag) as well as fragments which include a mutated HEXXH (SEQ ID NO: 45) site (e.g., SEQ ID NO: 4, 6, 8, 9, 10, 15, 16, 18, 19, or 21 with one or more mutations in the HEXXH (SEQ ID NO: 45) site), variants thereof, and nucleic acid molecules encoding such proteins (such as a cDNA molecule). In one example, a Tp0751 protein fragment (such as SEQ ID NO: 3, 4, 5, 6, 7, 8, 9, 10, 15, 16, 18, 19, or 21) is modified with polyethylene glycol or methoxy polyethylene glycol (PEGylation, such as for example to increase the half-life of the protein) or directly or indirectly (e.g., via a linker) fused to another peptide (such as diphtheria toxin, tetanus toxin, KLH, or a purification tag, such as a histidine tag (e.g., 6-His). For example, the disclosure provides isolated Tp0751 protein fragments that include a mutated HEXXH (SEQ ID NO: 45) site, or a sequence comprising at least 90%, at least 95%, or at least 99% sequence identity to any of SEQ ID NOS: 4, 5, 6, 8, 9, 10, 15, 16, 18, 19, or 21, for example a protein having 0 to 20 conservative amino acid substitutions. In some examples, such variants retain a mutated HEXXH (SEQ ID NO: 45) site, but have changes at other amino acids (e.g., in a variant protein having H121A in SEQ ID NO: 15 or 16 would not have the H121A substitution changed, or for example the following substitutions would not be changed: E175A of SEQ ID NO: 5, H178A of SEQ ID NO: 6, H175A of SEQ ID NO: 8, E176A of SEQ ID NO: 9, H179A of SEQ ID NO: 10, amino acids 174-178 of SEQ ID NO: 4, amino acids 174-178 of SEQ ID NO: 5, amino acids 174-178 of SEQ ID NO: 6, amino acids 175-179 of SEQ ID NO: 8, amino acids 175-179 of SEQ ID NO: 9, and/or amino acids 175-179 of SEQ ID NO: 10). Pharmaceutical compositions, such as a vaccine, which include one or more isolated Tp0751 protein fragments, isolated nucleic acid molecules that encode Tp0751 protein fragments, or vectors that include the nucleic acid, are provided. The disclosure also provides kits containing such Tp0751 protein fragments.

The foregoing and other objects and features of the disclosure will become more apparent from the following detailed description, which proceeds with reference to the accompanying figures.

BRIEF DESCRIPTION OF THE DRAWINGS

FIGS. 3A and 3B are line graphs showing the effect on (A) chancre ulceration and (B) chancre volume in rabbits immunized or not (control) with aa 24-237 of Tp0751 and subsequently challenged with *T. pallidum*.

FIG. 4A is a schematic of the primary structure of Tp0751, indicating the N-terminal signal peptide (SP), the putative thrombin cleavage site (Ser78), and the region with predicted secondary structure elements (Val99 to Lys228, boxed). FIG. 4B is a plot showing size exclusion chromatograms for constructs of Tp0751 (Tp0751_78A, 18 kDa; Tp0751_99A, 16 kDa) and globular standards (molecular weight in kDa listed above each peak) using a Superdex 75 HiLoad column. FIG. 4C shows the tertiary structure of Tp0751_78A, revealing an 8-stranded antiparallel beta-barrel capped by two helices. Note the most N-terminal residue modeled is Gln96. FIG. 4D is a digital image showing an SDS-PAGE gel, revealing that the complete Tp0751_78A construct is packed in the crystal.

FIG. 5A Left—Tertiary structure of Tp0751_78A. Key residues of SCR1 (W) and SCR3 (R) are highlighted by a blackbox. Right—Nitrophorin 4 (PDB ID 4KOI) shown in the same orientation and shading as Tp0751_78. N- and C-terminal disulfide bonds are shown as sticks and indicated by the starbursts. FIG. 5B Left—Sequences of SCR1 and SCR3 extracted from Tp0751 (aa 123-129 and 224-228 of SEQ ID NO: 2), Nitrophorin 4 (PDB ID 1KOI) (SEQ ID NO: 38), Triabin (PDB ID 1AVG) (SEQ ID NO: 39), MPI (metalloproteinase inhibitor, PDB ID 1SMP) (SEQ ID NO: 40), and hNGAL (Human neutrophil gelatinase-associated lipocalin, PDB ID 1NGL) (SEQ ID NO: 41). Key conserved residues are W and R shown in bold font. For the motif, H is hydrophobic and P is polar. Right—Sigma-A weighted 2Fo-Fc electron density map contoured at 1.2 sigma around the SCR1 and SCR3 motif Trp and Arg residues of Tp0751_78A. Dashed lines indicate 2.8 Å hydrogen bonds. FIG. 5C shows orthogonal views of the T0751_78A hydrophobic core. Residues that stack on the hydrophobic core at the open end are shown as sticks in the right panel, with the Trp-Met stack anchoring Loop 7 indicated by the black arrow. Note the absence of an accessible pocket in the open end.

FIGS. 6A-6C. Tp0751 peptides 4, 6, 10, and 11 bind host proteins. FIG. 6A is a bar graph showing binding of Tp0751 peptides p4, p6, p11, and p10scr to fibrinogen, fibronectin, collagen I, and collagen IV. FIG. 6B are a series of ribbon diagrams showing mapping of peptides p4, p6, p11, and p11 to the Tp0751 lipocalin domain. FIG. 6C shows sequences p4 (SEQ ID NO: 25), p6 (SEQ ID NO: 27), p10 (SEQ ID NO: 31), and p11 (SEQ ID NO: 32).

SEQUENCE LISTING

Figure 1:
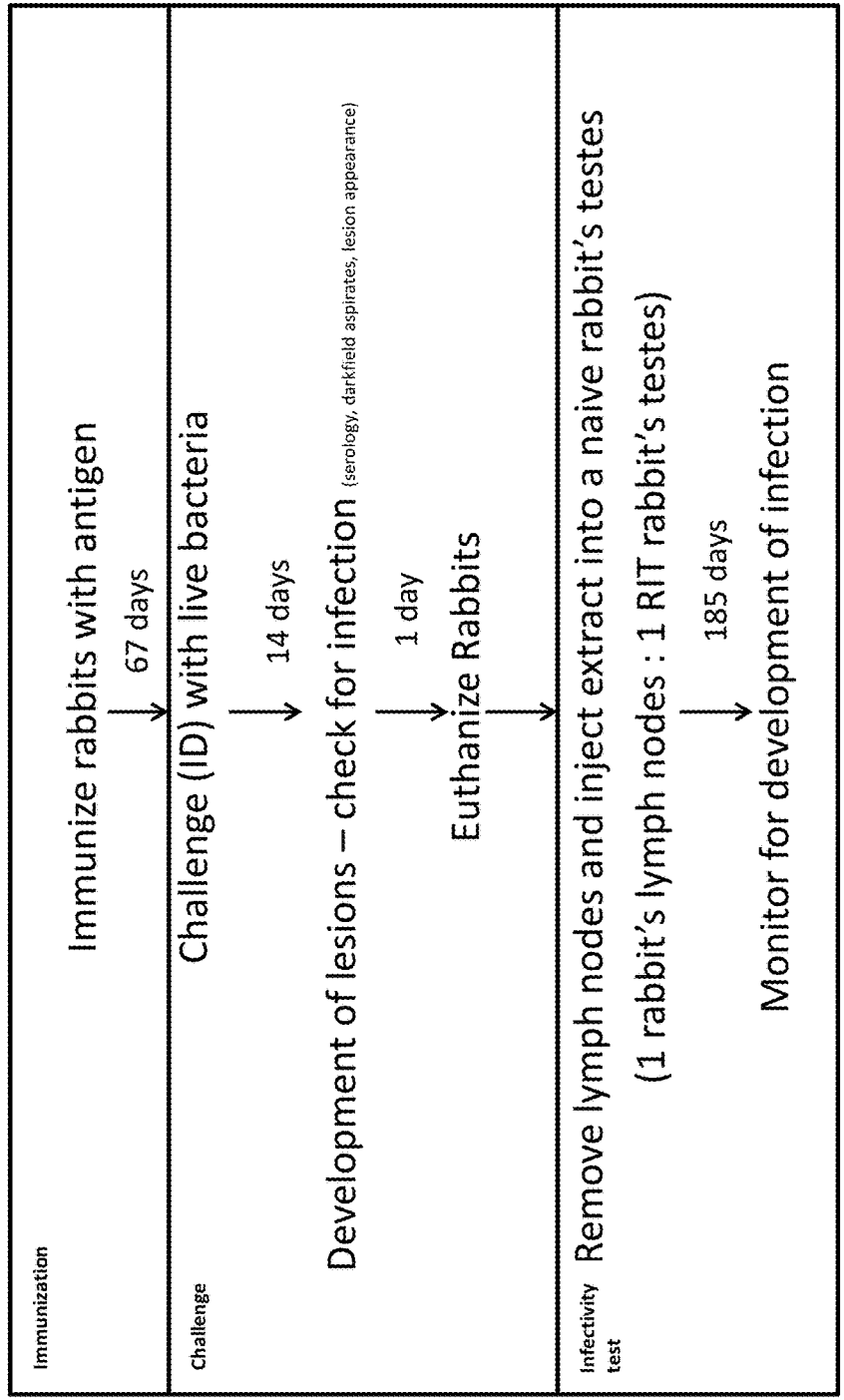
FIG. 1 provides an overview of the methods used to immunize rabbits and challenge them with *T. pallidum*.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 27, 2017, 42 KB, which is incorporated by reference herein. In the accompanying sequence listing:

SEQ ID NO: 1 is an exemplary Tp0751 coding sequence (nt 815821 . . . 816534 of GenBank Accession No. AE000520.1)

SEQ ID NO: 2 (GenBank Accession No. NP_219188) is an exemplary full-length Tp0751 amino acid sequence (with HEXXH (SEQ ID NO: 45) site at amino acids 198-202), which includes a signal sequence (amino acids 1-23) which are cleaved off to form the mature protein found in *T. pallidum.*

SEQ ID NO: 3 is a fragment of Tp0751 (aa 25-237) (native HEXXH (SEQ ID NO: 45) site at amino acids 174-178). This is encoded by nt 73-711 of SEQ ID NO: 1.

SEQ ID NO: 4 is a fragment of Tp0751 (aa 25-237) with a mutated HEXXH (SEQ ID NO: 45) site (H174A).

SEQ ID NO: 5 is a fragment of Tp0751 (aa 25-237) with a mutated HEXXH (SEQ ID NO: 45) site (E175A).

SEQ ID NO: 6 is a fragment of Tp0751 (aa 25-237) with a mutated HEXXH (SEQ ID NO: 45) site (H178A).

SEQ ID NO: 7 is a fragment of Tp0751 (aa 24-237) (native HEXXH (SEQ ID NO: 45) site at amino acids 175-179). This is encoded by nt 70-711 of SEQ ID NO: 1.

SEQ ID NO: 8 is a fragment of Tp0751 (aa 24-237) with a mutated HEXXH (SEQ ID NO: 45) site (H175A).

SEQ ID NO: 9 is a fragment of Tp0751 (aa 24-237) with a mutated HEXXH (SEQ ID NO: 45) site (E176A).

SEQ ID NO: 10 is a fragment of Tp0751 (aa 24-237) with a mutated HEXXH (SEQ ID NO: 45) site (H179A).

SEQ ID NOS: 11-13 are exemplary purification tags.

SEQ ID NOS: 14 and 15 are the coding and amino acid sequence of fragment Tp0751_S78-P237.

SEQ ID NO: 16 is the amino acid sequence of fragment Tp0751_S78-P237A (which includes an E199A mutation, wherein numbering is based on the full-length Tp0751 sequence).

SEQ ID NOS: 17 and 18 are the coding and amino acid sequence of fragment Tp0751_V99-P237.

SEQ ID NO: 19 is the amino acid sequence of fragment Tp0751_V99-P237A (which includes an E199A mutation, wherein numbering is based on the full-length Tp0751 sequence).

SEQ ID NOS: 20 and 21 are the coding and amino acid sequence of fragment Tp0751_E115-P237.

SEQ ID NO: 22 is peptide p1 of Tp0751.
SEQ ID NO: 23 is peptide p2 of Tp0751.
SEQ ID NO: 24 is peptide p3 of Tp0751.
SEQ ID NO: 25 is peptide p4 of Tp0751.
SEQ ID NO: 26 is peptide p5 of Tp0751.
SEQ ID NO: 27 is peptide p6 of Tp0751.
SEQ ID NO: 28 is peptide p7 of Tp0751.
SEQ ID NO: 29 is peptide p8 of Tp0751.
SEQ ID NO: 30 is peptide p9 of Tp0751.
SEQ ID NO: 31 is peptide p10 of Tp0751.
SEQ ID NO: 32 is peptide p11 of Tp0751.
SEQ ID NO: 33 is peptide p12 of Tp0751.
SEQ ID NO: 34 is peptide p13 of Tp0751.
SEQ ID NO: 35 is peptide p4scr.
SEQ ID NO: 36 is peptide p6scr.
SEQ ID NO: 37 is peptide p10scr.
SEQ ID NO: 38 is portion of a nitrophorin 4 sequence.
SEQ ID NO: 39 is portion of a triabin (PDB ID 1AVG) sequence.
SEQ ID NO: 40 is portion of a MPI (metalloproteinase inhibitor, PDB ID 1SMP) sequence.
SEQ ID NO: 41 is portion of an hNGAL (Human neutrophil gelatinase-associated lipocalin, PDB ID 1NGL) sequence.
SEQ ID NO: 42 is the amino acid sequence R-R-X-R/K.
SEQ ID NO: 43 is the amino acid sequence X-X-R/K-X-X.
SEQ ID NO: 44 is the amino acid sequence RxRxxR.
SEQ ID NO: 45 is the amino acid sequence HEXXR.

DETAILED DESCRIPTION

Detailed Description of Several Embodiments

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a Tp0751 fragment" includes single or plural Tp0751 fragments and is considered equivalent to the phrase "comprising at least one Tp0751 fragment." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All GenBank accession numbers and references provided herein are incorporated by reference.

Adjuvant: A vehicle used to enhance antigenicity. Adjuvants which can be used in combination with the Tp0751 fragments disclosed herein (including the mutated and modified Tp0751 fragments disclosed herein) include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199). Adjuvants include biological molecules (a "biological adjuvant"), such as costimulatory molecules. Other exemplary adjuvants include IL-2, RANTES, GM-CSF, TNF-α, IFN-γ, G-CSF, LFA-3, CD72, B7-1, B7-2, OX-40L and 4-1 BBL. Other exemplary adjuvants include chitosan, *Bacillus*-Calmette-Guerin adjuvant and RIBI adjuvant. Other adjuvants are disclosed herein. Thus, one or more of these adjuvants can be included in the pharmaceutical compositions provided herein that contain one or more Tp0751 fragments.

Antigen: A compound, composition, or substance that can stimulate the production of antibodies or a T cell response in an animal, including compositions that are injected or absorbed into an animal. An exemplary antigen is a native or non-native fragment of Tp0751, (which can optionally include a tag at the N- or C-terminus, such as a 6×His tag or other purification tag), as well as a modified Tp0751 protein fragment (such as one modified with polyethylene glycol or methoxy polyethylene glycol (PEGylation) or one directly or indirectly fused to another peptide such as diphtheria toxin, tetanus toxin, KLH, or a purification tag. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation, but is generally not more than 20 amino acids in length. Methods of determining spatial conformation of epitopes include, for example, x-ray crystallography and 2-dimensional nuclear magnetic resonance.

Antibody: Immunoglobulin molecules and immunologically active portions of immunoglobulin molecules, i.e., molecules that contain an antigen binding site that specifically binds (immunoreacts with) an antigen, such as a fragment of a Tp0751 protein provided herein.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., Nature 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984). Humanized antibodies and fully human antibodies are also known in the art.

Consists Essentially Of/Consists Of: With regard to a protein (such as a native or non-native fragment of Tp0751), a protein that consists essentially of a specified amino acid sequence if it does not include any additional amino acid residues. However, the protein can include additional non-peptide components, such as labels (for example, fluorescent, radioactive, or solid particle labels), PEG, sugars or lipids. With regard to a protein that consists of a specified amino acid sequence does not include any additional amino acid residues, nor does it include additional non-peptide components, such as lipids, PEG, sugars or labels.

Degenerate variant: A polynucleotide encoding fragment of Tp0751 that includes a sequence that is degenerate as a result of the genetic code. There are 20 natural amino acids, most of which are specified by more than one codon. Therefore, all degenerate nucleotide sequences are included in this disclosure as long as the amino acid sequence of the fragment of Tp0751 protein encoded by the nucleotide sequence is unchanged.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies (such as T. pallidum- or Tp0751-specific antibodies).

Immunogenic composition: A composition, such as a composition comprising a native or non-native fragment of Tp0751 protein or a nucleic acid encoding the native or non-native fragment of Tp0751, that induces a measurable T cell response against cells expressing Tp0751 protein, or induces a measurable B cell response (such as production of antibodies that specifically bind Tp0751) against a Tp0751 protein. For in vitro use, the immunogenic composition can consist of the isolated nucleic acid, vector including the nucleic acid/or immunogenic protein. For in vivo use, the immunogenic composition will typically include the nucleic acid, vector including the nucleic acid, and or immunogenic protein, in pharmaceutically acceptable carriers, and/or other agents. An immunogenic composition can optionally include an adjuvant, a costimulatory molecule, a nucleic acid encoding a costimulatory molecule, or combinations thereof.

Immunogenic Protein: A protein which includes an allele-specific motif or other sequence such that the peptide will bind an MHC molecule and induce a T cell response, or a B cell response (e.g., antibody production) against the antigen. An exemplary immunogenic protein is a native or non-native fragment of Tp0751 (such as SEQ ID NO: 3, 4, 5, 6, 7, 8, 9, 10, 15, 16, 18, 19, or 21, for example with a mutation in the HEXXH (SEQ ID NO: 45) active site, or shorter immunogenic fragments thereof).

Immunogenic fragments of native or non-native Tp0751 cause induction of an immune response, as measured by clinical response (for example an increase in a population of immune cells, increased cytolytic activity against cells that express Tp0751, increased production of Tp0751 antibodies, or measurable reduction of chancre volume or ulcerations, or combinations thereof). Immunogenic proteins can also be made from nucleic acids. Examples of a nucleic acid based therapeutically active molecule is a nucleic acid sequence that encodes a native or non-native Tp0751 protein fragment, wherein the nucleic acid sequence is operably linked to a control element such as a promoter.

Isolated: A biological component (such as a nucleic acid molecule or protein) that has been substantially separated, produced apart from, or purified away from other biological components in the cell of the organism in which the component naturally occurs, such as other chromosomal and extrachromosomal DNA and RNA, and proteins. Nucleic acid molecules and proteins which have been "isolated" include nucleic acid molecules and proteins purified by standard purification methods. The term also includes nucleic acid molecules and proteins prepared by recombinant expression in a host cell as well as chemically synthesized nucleic acid molecules and peptides. For example, an isolated or "purified" Tp0751 protein or fragment thereof can be substantially free of other proteins, lipids, carbohydrates or other materials with which it was associated. In one embodiment, a Tp0751 protein fragment is at least 50%, for example at least 80%, at least 90%, or at least 95% free of other proteins, lipids, carbohydrates or other materials with which it was associated (such as a cell lysate).

pDEST17: A gateway expression vector that is used in universal cloning techniques allowing the transfer of DNA between different cloning vectors while maintaining the reading frame, designed by Invitrogen Life Technologies, Cat. No. 11803012.

Peptide Modifications: The Tp0751 protein fragments provided include synthetic embodiments of polypeptides described herein. In addition, analogs (non-peptide organic molecules), derivatives (chemically functionalized polypeptide molecules obtained starting with the disclosed Tp0751 protein fragments) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified polypeptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the polypeptide side chains may be converted to $C_1$-$C_{16}$ alkoxy or to a $C_1$-$C_{16}$ ester using well-recognized techniques. Phenyl and phenolic rings of the polypeptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the polypeptide backbone and component amino acid side chains, resulting in such peptido- and organomimetics of Tp0751 protein fragments having measurable or enhanced ability to stimulate an immune response. For computer modeling applications, a pharmacophore is an idealized three-dimensional definition of the structural requirements for biological activity. Peptido- and organomimetics can be designed to fit each pharmacophore with computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the native or non-native Tp0751 protein fragments herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired effect in a subject being treated. For instance, this can be the amount of a native or non-native Tp0751 protein fragment or a vector encoding such a protein, necessary to induce an immune response, reduce chancre volume (e.g., relative to no administration of the native or non-native Tp0751 protein fragment), reduce the % of chancres that ulcerate (e.g., relative to no administration of the native or non-native Tp0751 protein fragment), reduce orchitis (e.g., relative to no administration of the native or non-native Tp0751 protein fragment), reduce dissemination of *T. pallidum* to lymph nodes and other tissues and organs (e.g., relative to no administration of the native or non-native Tp0751 protein fragment), measurably improve outward symptoms of a *T. pallidum* infection (e.g., relative to no administration of the native or non-native Tp0751 protein fragment), or combinations thereof. When administered to a subject, a dosage will generally be used that will achieve target tissue concentrations (for example, in lymphocytes) that has been shown to achieve an in vitro effect.

Recombinant: A recombinant protein or nucleic acid is one that has a sequence that is not naturally occurring or has a sequence that is made by an artificial combination of two otherwise separated segments of sequence. This artificial combination can accomplished by chemical synthesis or other methods known in the art, such as by the artificial manipulation of isolated segments of nucleic acids, e.g., by genetic engineering techniques.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.*

48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 15-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 30% sequence identity or more counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity with a Tp0751 protein, or fragments thereof. Thus in one example, a Tp0751 protein fragment has at least 60%, at least 70%, at least 80%, at least 90%, at least 95%, at least 98%, or at least 99% sequence identity to SEQ ID NO: 3, 4, 5, 6, 7, 8, 9, 10, 15, 16, 18, 19, or 21 and retains the ability to stimulate an immune response against Tp0751 in vivo.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity with a Tp0751 sequence as determined by this method. Thus in one example, a Tp0751 nucleic acid encoding sequence has at least 60%, at least 70%, at least 80%, at least 90%, at least 95%, at least 98%, or at least 99% sequence identity to SEQ ID NO: 1, 14, 17, or 20, or nucleotides 70-711 or 73-711 of SEQ ID NO: 1, and encodes a native or non-native Tp0751 protein or fragment thereof (such as SEQ ID NO: 3, 4, 5, 6, 7, 8, 9, 10, 15, 16, 18, 19, or 21). An alternative (and not necessarily cumulative) indication that two nucleic acid sequences are substantially identical is that the polypeptide which the first nucleic acid encodes is immunologically cross reactive with the polypeptide encoded by the second nucleic acid;

Subject: Living multi-cellular vertebrate organisms, a category that includes human and non-human mammals, for example mammals that get syphilis (such as humans and rabbits).

Tp0751 (also known as pallilysin): A surface antigen of *T. pallidum*, which has been reported previously to bind to laminin. Antibodies against this adhesin are present in serum from both natural and experimental *T. pallidum* infections. The term Tp0751 includes a Tp0751 gene, cDNA, mRNA, or protein. Nucleic acid and protein sequences for Tp0751 are publicly available. For example, nt 815821 . . . 816534 of GenBank Accession No. AE000520.1 discloses a Tp0751 nucleic acid coding sequence, and GenBank Accession Nos.: NP_219188.1 and AAC65720.1 disclose Tp0751 protein sequences, all of which are incorporated by reference as provided by GenBank on Jan. 12, 2016.

Tp0751 begins as pre-protein (e.g., SEQ ID NO: 2), from which a mature protein found in *T. pallidum* is generated by cleaving off the signal sequence (amino acids 1-23). Fragments of Tp0751 refer to native fragments of the pre-protein or the mature protein (e.g., SEQ ID NO: 3 7, 15, 18, or 21) as well as non-native fragments containing a mutated HEXXH (SEQ ID NO: 45) site (e.g., SEQ ID NO: 4, 5, 6, 8, 9, 10, 16 or 19). One skilled in the art will appreciate that variations can be made to these sequences, as long as the Tp0751 protein fragment can stimulate an immune response in vivo. In certain examples, a variant Tp0751 protein fragment has at least 80% sequence identity, for example at least 85%, at least 90%, at least 95%, at least 97%, at least 98%, or at least 99% sequence identity to SEQ ID NO: 3, 4, 5, 6, 7, 8, 9, 10, 15, 16, 18, 19, or 21 and can stimulate an immune response in vivo, for example a protective immune response against *T. pallidum* infection. In one example, a Tp0751 protein fragment (such as SEQ ID NO: 3, 4, 5, 6, 7, 8, 9, 10, 15, 16, 18, 19, or 21) can contain 1 to 20 conservative amino acid substitutions, and can further include a tag, such as purification tag, such as an N-terminal or C-terminal histidine tag (such as a histidine tag having 3 to 6 histidine residues, such as 3-, 4-, 5- or 6-His).

In some examples, a variant non-native Tp0751 protein fragment includes a mutated HEXXH (SEQ ID NO: 45) site, but has changes at one or more other amino acids, such as conservative or non-conservative changes to 1 to 20, 1 to 10, or 1 to 5 amino acids. For example, a variant non-native Tp0751 protein fragment that retains the mutated HEXXH (SEQ ID NO: 45) site can retain an H121A, E122A, and/or H125A mutation in SEQ ID NO: 15 or 16, an H100A, E101A, and/or H104A mutation in of SEQ ID NO: 18 or 19, an H84A, E85A, and/or H88A mutation in SEQ ID NO: 21, an H174A mutation in SEQ ID NO: 4, an E175 mutation in SEQ ID NO: 5, an H178A mutation in SEQ ID NO: 6, an H175A mutation in SEQ ID NO: 8, an E176A mutation in SEQ ID NO: 9, an H179A mutation in SEQ ID NO: 10, amino acids 174-178 of SEQ ID NO: 4, amino acids 174-178 of SEQ ID NO: 5, amino acids 174-178 of SEQ ID NO: 6, amino acids 175-179 of SEQ ID NO: 8, amino acids 175-179 of SEQ ID NO: 9, and/or amino acids 175-179 of SEQ ID NO: 10, but include mutations at one or more other amino acid positions (that is, these sequences would not be changed in the variant peptide, e.g., one having at least 80%, at least 90%, at least 95% etc. sequence identity to SEQ ID NO: 4, 5, 6, 8, 9, 10, 15, 16, 17, 18, 19, or 21).

Immunogenic Tp0751 Protein Fragments and Coding Sequences

Proteins

The present disclosure provides isolated or purified Tp0751 fragments, such as native sequences shown in SEQ ID NO: 3 and 7, amino acids 78-237 of SEQ ID NO: 2, amino acids 79-237 of SEQ ID NO: 2, amino acids 80-237 of SEQ ID NO: 2, amino acids 81-237 of SEQ ID NO: 2, amino acids 82-237 of SEQ ID NO: 2, amino acids 83-237 of SEQ ID NO: 2, amino acids 84-237 of SEQ ID NO: 2, amino acids 85-237 of SEQ ID NO: 2, amino acids 86-237 of SEQ ID NO: 2, amino acids 87-237 of SEQ ID NO: 2, amino acids 88-237 of SEQ ID NO: 2, amino acids 89-237 of SEQ ID NO: 2, amino acids 90-237 of SEQ ID NO: 2, amino acids 91-237 of SEQ ID NO: 2, amino acids 92-237 of SEQ ID NO: 2, amino acids 93-237 of SEQ ID NO: 2, amino acids 94-237 of SEQ ID NO: 2, amino acids 95-237 of SEQ ID NO: 2, amino acids 96-237 of SEQ ID NO: 2, amino acids 97-237 of SEQ ID NO: 2, amino acids 98-237 of SEQ ID NO: 2, amino acids 99-237 of SEQ ID NO: 2, amino acids 100-237 of SEQ ID NO: 2, amino acids 101-237 of SEQ ID NO: 2, amino acids 102-237 of SEQ ID NO: 2, amino acids 103-237 of SEQ ID NO: 2, amino acids 104-237 of SEQ ID NO: 2, amino acids 105-237 of SEQ ID NO: 2, amino acids 106-237 of SEQ ID NO: 2, amino acids 107-237 of SEQ ID NO: 2, amino acids 108-237 of SEQ ID NO: 2, amino acids 109-237 of SEQ ID NO: 2, amino acids 110-237 of SEQ ID NO: 2, amino acids 111-237 of SEQ ID NO: 2, amino acids 112-237 of SEQ ID NO: 2, amino acids 113-237 of SEQ ID NO: 2, amino acids 114-237 of SEQ ID NO: 2, amino acids 115-237 of SEQ ID NO: 2, as well as non-native fragments that include one or more mutations in the HEXXH (SEQ ID NO: 45) site of these fragments (native site is HEXXH (SEQ ID NO: 45), so 1, 2, or all 3 of H1, E2 or H5 can be mutated in each of these Tp0751 fragments, for example mutated to an alanine), such as those shown in SEQ ID NOs: 4-6 and 8-10. In some examples, these Tp0751 proteins and fragments include other mutations, such as an alanine at position 46, 78, 92, 199 or combinations thereof (wherein the numbering is relative to SEQ ID NO: 2), such as at 1, 2, 3, or all 4 of these positions. For example, a variant non-native Tp0751 protein fragment can retain a mutated HEXXH (SEQ ID NO: 45) site, but have changes at one or more other amino acids, such as conservative or non-conservative changes to 1 to 20, 1 to 10, or 1 to 5 amino acids. For example, a variant non-native Tp0751 protein fragment that retains the mutated HEXXH (SEQ ID NO: 45) site can retain H121A, E122A, and/or H125A mutation in SEQ ID NO: 15 or 16, an H100A, E101A, and/or H104A mutation of SEQ ID NO: 18 or 19, an H84A, E85A, and/or H88A mutation in SEQ ID NO: 21, an H174A mutation in SEQ ID NO: 4, an E175 mutation in SEQ ID NO: 5, an H178A mutation in SEQ ID NO: 6, an H175A mutation in SEQ ID NO: 8, an E176A mutation in SEQ ID NO: 9, an H179A mutation in SEQ ID NO: 10, amino acids 174-178 of SEQ ID NO: 4, amino acids 174-178 of SEQ ID NO: 5, amino acids 174-178 of SEQ ID NO: 6, amino acids 175-179 of SEQ ID NO: 8, amino acids 175-179 of SEQ ID NO: 9, and/or amino acids 175-179 of SEQ ID NO: 10 (that is, these mutations could be made to SEQ ID NO: 4, 5, 6, 8, 9, 10, 15, 16, 18, 19, or 21, along with one or other mutations, to achieve a variant protein having at least 80%, at least 90%, at least 95% etc. sequence identity to SEQ ID NO: 4, 5, 6, 8, 9, 10, 15, 16, 18, 19, or 21).

In some examples, a Tp0751 fragment includes the C-terminal end of the mature Tp0751 protein, such as one that includes at least 30, at least 35, at least 40, at least 45, at least 50, least 55, at least 60, at least 70, at least 80, at least 90, at least 100, at least 110, at least 115, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, least 150, at least 151, at least 152, at least 153, at least 154, at least 155, at least 156, at least 157, at least 158, at least 159, or at least 160 consecutive C-terminal amino acids (such as the region of amino acids 150-237, 180-237, or 190-237 of SEQ ID NO: 2, or such as amino acids 79-237 of SEQ ID NO: 2, amino acids 80-237 of SEQ ID NO: 2, amino acids 81-237 of SEQ ID NO: 2, amino acids 82-237 of SEQ ID NO: 2, amino acids 83-237 of SEQ ID NO: 2, amino acids 84-237 of SEQ ID NO: 2, amino acids 85-237 of SEQ ID NO: 2, amino acids 86-237 of SEQ ID NO: 2, amino acids 87-237 of SEQ ID NO: 2, amino acids 88-237 of SEQ ID NO: 2, amino acids 89-237 of SEQ ID NO: 2, amino acids 90-237 of SEQ ID NO: 2, amino acids 91-237 of SEQ ID NO: 2, amino acids 92-237 of SEQ ID NO: 2, amino acids 93-237 of SEQ ID NO: 2, amino acids 94-237 of SEQ ID NO: 2, amino acids 95-237 of SEQ ID NO: 2, amino acids 96-237 of SEQ ID NO: 2, amino acids 97-237 of SEQ ID NO: 2, amino acids 98-237 of SEQ ID NO: 2, amino acids 99-237 of SEQ ID NO: 2, amino acids 100-237 of SEQ ID NO: 2, amino acids 101-237 of SEQ ID NO: 2, amino acids 102-237 of SEQ ID NO: 2, amino acids 103-237 of SEQ ID NO: 2, amino acids 104-237 of SEQ ID NO: 2, amino acids 105-237 of SEQ ID NO: 2, amino acids 106-237 of SEQ ID NO: 2, amino acids 107-237 of SEQ ID NO: 2, amino acids 108-237 of SEQ ID NO: 2, amino acids 109-237 of SEQ ID NO: 2, amino acids 110-237 of SEQ ID NO: 2, amino acids 111-237 of SEQ ID NO: 2, amino acids 112-237 of SEQ ID NO: 2, amino acids 113-237 of SEQ ID NO: 2, amino acids 114-237 of SEQ ID NO: 2, amino acids 115-237 of SEQ ID NO: 2) (as removing the C-terminal end can result in insoluble expression). In one example, the Tp0751 fragment includes the HEXXH (SEQ ID NO: 45) site within the C terminus of the protein. In other examples, the HEXXH (SEQ ID NO: 45) site within the C terminus of the protein is mutated as discussed herein, for example by mutating H1, E2, H5, or combinations thereof.

These Tp0751 fragments can be used as an immunogen, such as a vaccine, in the methods provided herein. Thus, the Tp0751 fragments disclosed herein can be used to induce an immune response (are immunogenic), wherein the Tp0751 fragment can produce a Tp0751-specific CD4+ T cell response. In some embodiments, the Tp0751 fragment produces a Tp0751-specific B cell response, a Tp0751-specific CD4+ T cell response, a Tp0751-specific CD8+ T cell response, or combinations thereof. For example, such Tp0751 fragments can be used to illicit a B cell response (e.g., production of serum antibodies which have neutralizing activity for *T. pallidum*), and thus can be used as a vaccine against *T. pallidum* infection.

One skilled in the art will recognize that such sequences can be altered using routine methods in the art (such as recombinant molecular biology methods), while not significantly decreasing the desired activity of the Tp0751 protein fragment, such as the ability to produce an immune response (e.g., generate antibodies specific for Tp0751, such as those having neutralizing activity for *T. pallidum*) when administered to a mammal. The immunogenicity of a Tp0751 protein fragment variant can be assessed by determining whether it is recognized by Tp0751 antibodies (such as Tp0751 antibodies present in a subject having syphilis). In some examples, a Tp0751 protein fragment binds MHC Class II, such as one encoded by a HLA-DP, HLA-DR, HLA-B, HLA-DQA1 or HLA-DQB1 allele.

Thus, the present disclosure provides variants of the disclosed Tp0751 fragment sequences, such as a Tp0751 fragment sequence having at least 60%, at least 70%, at least 80%, at least 90%, at least 91%, at least 92%, at least 93%, at least 94%, at least 95%, at least 96%, at least 97%, at least 98%, or at least 99% sequence identity to SEQ ID NO: 3, 4, 5, 6, 7, 8, 9, 10, 15, 16, 18, 19, or 21, such as or such identity to a protein comprising or consisting of amino acids 78-237 of SEQ ID NO: 2. In one example, a Tp0751 fragment includes, consists of, or consists essentially of, an amino acid sequence at least at least 90% identical to SEQ ID NO: 3, 4, 5, 6, 7, 8, 9, 10, 15, 16, 18, 19, or 21, for example a polypeptide that is about 91%, 92%, 93%, 94%, 95%, 96%, 97%, 98% or 99% identical to SEQ ID NO: 3, 4, 5, 6, 7, 8, 9, 10, 15, 16, 18, 19, or 21. In some examples, such a protein is no more than 180 amino acids long, no more than 170 amino acids long, no more than 160 amino acids long, no more than 150 amino acids long, no more than 145 amino acids long, no more than 140 amino acids long, no more than 139 amino acids long, no more than 135 amino acids long, no more than 125 amino acids long, no more than 123 amino acids long, or no more than 120 amino acids long, such as 120 to 180 aa, 120 to 170 aa, or 123-160 aa. For example, the peptide sequence shown in SEQ ID NO: 3, 4, 5, 6, 7, 8, 9, 10, 15, 16, 18, 19, or 21 can be modified by making one or more conservative amino acid substitutions, such as 1 to 20, 1 to 15, 1 to 12, 1 to 10, or 1 to 5 conservative amino acid substitutions, such as 1, 2, 3, 4, 5, 6, 7, 8, 9, 10, 11, 12, 13, 14, 15, 16, 17, 18, 19, or 20 conservative amino acid substitutions, while retaining the ability to produce an immune response when administered to a mammal. In some examples, amino acids 121, 122, and/or 125 of SEQ ID NO: 15 or 16, amino acids 100, 101, and/or 104 of SEQ ID NO: 18 or 19, or amino acids 184, 85, and/or 88 of SEQ ID NO: 21, are changed (for example to an alanine). In some examples amino acids 174, 175 and 178 of SEQ ID NOS: 4-6, respectively (such as any or all of amino acids 174-178) are not changed. In some examples amino acids 175, 176 and 177 of SEQ ID NOS: 8-10, respectively (such as any or all of amino acids 175-176) are not changed. In one example, a variant non-native Tp0751 protein fragment that retains the mutated HEXXH (SEQ ID NO: 45) site can retain H174A of SEQ ID NO: 4, E175A of SEQ ID NO: 5, H178A of SEQ ID NO: 6, H175A of SEQ ID NO: 8, E176A of SEQ ID NO: 9, H179A of SEQ ID NO: 10, amino acids 174-178 of SEQ ID NO: 4, amino acids 174-178 of SEQ ID NO: 5, amino acids 174-178 of SEQ ID NO: 6, amino acids 175-179 of SEQ ID NO: 8, amino acids 175-179 of SEQ ID NO: 9, and/or amino acids 175-179 of SEQ ID NO: 10 (that is, these sequences would not be changed in the variant peptide, e.g., one having at least 80%, at least 90%, at least 95% etc. sequence identity to SEQ ID NO: 4, 5, 6, 8, 9, or 10).

Examples of conservative substitutions are shown in Table 1:

TABLE 1

Exemplary conservative amino acid substitutions

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Such substitutions can be made to any Tp0751 protein or fragment herein provided.

In some examples, a Tp0751 fragment includes at least at least 15, at least 20, at least 30, at least 40, at least 50, at least 60, at least 70, at least 80, at least 90, at least 100, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, least 150, at least 151, at least 152, at least 153, at least 154, at least 155, at least 156, at least 157, at least 158, at least 159, at least 160, at least 200, at least 210, or at least 220 amino acids of a full-length Tp0751 protein (e.g., SEQ ID NO: 2). The Tp0751 fragment can include 15, 20, 30, 40, 50, 60, 70, 80, 90, 100, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 200, 210, 212, 213, or 220 contiguous amino acids of a full-length Tp0751 protein (e.g., SEQ ID NO: 2). In some embodiments, a Tp0751 fragment is 15-212, 20-212, 30-212, 40-212, 50-212, 60-212, 70-212, 80-212, 90-212, 100-212, or 200-212 amino acids of a full-length Tp0751 protein (e.g., SEQ ID NO: 2). In other embodiments, a Tp0751 fragment is 15-213, 20-213, 30-213, 40-213, 50-213, 60-213, 70-213, 80-213, 90-213, 100-213, or 200-213 amino acids of a full-length Tp0751 protein (e.g., SEQ ID NO: 2). In some embodiments, a Tp0751 fragment comprises or consists of amino acids 79-237 of SEQ ID NO: 2, amino acids 80-237 of SEQ ID NO: 2, amino acids 81-237 of SEQ ID NO: 2, amino acids 82-237 of SEQ ID NO: 2, amino acids 83-237 of SEQ ID NO: 2, amino acids 84-237 of SEQ ID NO: 2, amino acids 85-237 of SEQ ID NO: 2, amino acids 86-237 of SEQ ID NO: 2, amino acids 87-237 of SEQ ID NO: 2, amino acids 88-237 of SEQ ID NO: 2, amino acids 89-237 of SEQ ID NO: 2, amino acids 90-237 of SEQ ID NO: 2, amino acids 91-237 of SEQ ID NO: 2, amino acids 92-237 of SEQ ID NO: 2, amino acids 93-237 of SEQ ID NO: 2, amino acids 94-237 of SEQ ID NO: 2, amino acids 95-237 of SEQ ID NO: 2, amino acids 96-237 of SEQ ID NO: 2, amino acids 97-237 of SEQ ID NO: 2, amino acids 98-237 of SEQ ID NO: 2, amino acids 99-237 of SEQ ID NO: 2, amino acids 100-237 of SEQ ID NO: 2, amino acids 101-237 of SEQ ID NO: 2, amino acids 102-237 of SEQ ID NO: 2, amino acids 103-237 of SEQ ID NO: 2, amino acids 104-237 of SEQ ID NO: 2, amino acids 105-237 of SEQ ID NO: 2, amino acids 106-237 of SEQ ID NO: 2, amino acids 107-237 of SEQ ID NO: 2, amino acids 108-237 of SEQ ID NO: 2, amino acids 109-237 of SEQ ID NO: 2, amino acids 110-237 of SEQ ID NO: 2, amino acids 111-237 of SEQ ID NO: 2, amino acids 112-237 of SEQ ID NO: 2, amino acids 113-237 of SEQ ID NO: 2, amino acids 114-237 of SEQ ID NO: 2, amino acids 115-237 of SEQ ID NO: 2.

In one example, a Tp0751 fragment is part of a fusion protein. Such a fusion protein can include the Tp0751 fragment provided herein and a second heterologous moiety, such as a myc protein, KLH, a toxin (e.g., DT, tetanus), an enzyme or a carrier (such as a hepatitis carrier protein or bovine serum albumin) covalently linked to the Tp0751 fragment. When bound to a carrier, the Tp0751 fragment becomes more immunogenic. Carriers can increase the immunogenicity of the bound molecule and/or to elicit higher titers of antibodies against the carrier which are therapeutically beneficial. Covalent linking of a molecule to a carrier can confer enhanced immunogenicity and T cell dependence (see Pozsgay et al., PNAS 96:5194-97, 1999; Lee et al., J. Immunol. 116:1711-18, 1976; Dintzis et al., PNAS 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin (KLH), horseshoe crab hemocyanin, edestin, mammalian serum albumins, and mammalian immunoglobulins. Suitable carriers include, but are not limited to, a hepatitis B small envelope protein HBsAg. This protein has the capacity to self-assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317:489, 1985, and European Patent Publication No. EP-A-0 278 940, and PCT Publication No. WO 91/14703.

In some examples, a Tp0751 fragment (such as any of SEQ ID NOS: 3-10, amino acids 79-237 of SEQ ID NO: 2, amino acids 80-237 of SEQ ID NO: 2, amino acids 81-237 of SEQ ID NO: 2, amino acids 82-237 of SEQ ID NO: 2, amino acids 83-237 of SEQ ID NO: 2, amino acids 84-237 of SEQ ID NO: 2, amino acids 85-237 of SEQ ID NO: 2, amino acids 86-237 of SEQ ID NO: 2, amino acids 87-237 of SEQ ID NO: 2, amino acids 88-237 of SEQ ID NO: 2, amino acids 89-237 of SEQ ID NO: 2, amino acids 90-237 of SEQ ID NO: 2, amino acids 91-237 of SEQ ID NO: 2, amino acids 92-237 of SEQ ID NO: 2, amino acids 93-237 of SEQ ID NO: 2, amino acids 94-237 of SEQ ID NO: 2, amino acids 95-237 of SEQ ID NO: 2, amino acids 96-237 of SEQ ID NO: 2, amino acids 97-237 of SEQ ID NO: 2, amino acids 98-237 of SEQ ID NO: 2, amino acids 99-237 of SEQ ID NO: 2, amino acids 100-237 of SEQ ID NO: 2, amino acids 101-237 of SEQ ID NO: 2, amino acids 102-237 of SEQ ID NO: 2, amino acids 103-237 of SEQ ID NO: 2, amino acids 104-237 of SEQ ID NO: 2, amino acids 105-237 of SEQ ID NO: 2, amino acids 106-237 of SEQ ID NO: 2, amino acids 107-237 of SEQ ID NO: 2, amino acids 108-237 of SEQ ID NO: 2, amino acids 109-237 of SEQ ID NO: 2, amino acids 110-237 of SEQ ID NO: 2, amino acids 111-237 of SEQ ID NO: 2, amino acids 112-237 of SEQ ID NO: 2, amino acids 113-237 of SEQ ID NO: 2, amino acids 114-237 of SEQ ID NO: 2, amino acids 115-237 of SEQ ID NO: 2, or a variant having at least 90%, at least 92%, at least 95%, at least 98%, or at least 99% sequence identity to such sequences) includes a tag (for example to assist in purification of the protein), such as a C-terminal or N-terminal tag, such as an N-terminal histidine tag. In some examples, the tag is included to aid or permit isolation of the protein, and may or may not be removed before the use of the Tp0751 protein fragment as an immunogen. In some examples, the purification tag is about 3-20 amino acids in length, such as 3 to 10 or 4-6 amino acids. In one example the purification tag is a polyhistidine tag, such as 6-His, which permits nickel purification. Other exemplary purification tags that can be used include but are not limited to: glutathione-S-transferase (GST), a myc-Tag (EQKLISEED; SEQ ID NO: 11), FLAG-Tag (DYKDDDDK; SEQ ID NO: 12), HA-tag, S-tag (Lys-Glu-Thr-Ala-Ala-Ala-Lys-Phe-Glu-Arg-Gln-His-Met-Asp-Ser; SEQ ID NO: 13), and streptavidin. Thus, in some examples, the fusion protein includes a Tp0751 fragment and six sequential histidine residues, a β-galactosidase amino acid sequence, and/or an immunoglobulin amino acid sequence.

In some examples, a Tp0751 fragment (such as any of SEQ ID NOS: 3-10, amino acids 79-237 of SEQ ID NO: 2, amino acids 80-237 of SEQ ID NO: 2, amino acids 81-237 of SEQ ID NO: 2, amino acids 82-237 of SEQ ID NO: 2, amino acids 83-237 of SEQ ID NO: 2, amino acids 84-237 of SEQ ID NO: 2, amino acids 85-237 of SEQ ID NO: 2, amino acids 86-237 of SEQ ID NO: 2, amino acids 87-237 of SEQ ID NO: 2, amino acids 88-237 of SEQ ID NO: 2, amino acids 89-237 of SEQ ID NO: 2, amino acids 90-237 of SEQ ID NO: 2, amino acids 91-237 of SEQ ID NO: 2, amino acids 92-237 of SEQ ID NO: 2, amino acids 93-237 of SEQ ID NO: 2, amino acids 94-237 of SEQ ID NO: 2, amino acids 95-237 of SEQ ID NO: 2, amino acids 96-237 of SEQ ID NO: 2, amino acids 97-237 of SEQ ID NO: 2, amino acids 98-237 of SEQ ID NO: 2, amino acids 99-237 of SEQ ID NO: 2, amino acids 100-237 of SEQ ID NO: 2, amino acids 101-237 of SEQ ID NO: 2, amino acids 102-237 of SEQ ID NO: 2, amino acids 103-237 of SEQ ID NO: 2, amino acids 104-237 of SEQ ID NO: 2, amino acids 105-237 of SEQ ID NO: 2, amino acids 106-237 of SEQ ID NO: 2, amino acids 107-237 of SEQ ID NO: 2, amino acids 108-237 of SEQ ID NO: 2, amino acids 109-237 of SEQ ID NO: 2, amino acids 110-237 of SEQ ID NO: 2, amino acids 111-237 of SEQ ID NO: 2, amino acids 112-237 of SEQ ID NO: 2, amino acids 113-237 of SEQ ID NO: 2, amino acids 114-237 of SEQ ID NO: 2, amino acids 115-237 of SEQ ID NO: 2, or a variant having at least 90%, at least 92%, at least 95%, at least 98%, or at least 99% sequence identity to such) is modified such that it is not naturally occurring, for example amidated, myrisolted, pegylated, glycosylated, acetylated, and the like.

Figure 5A:
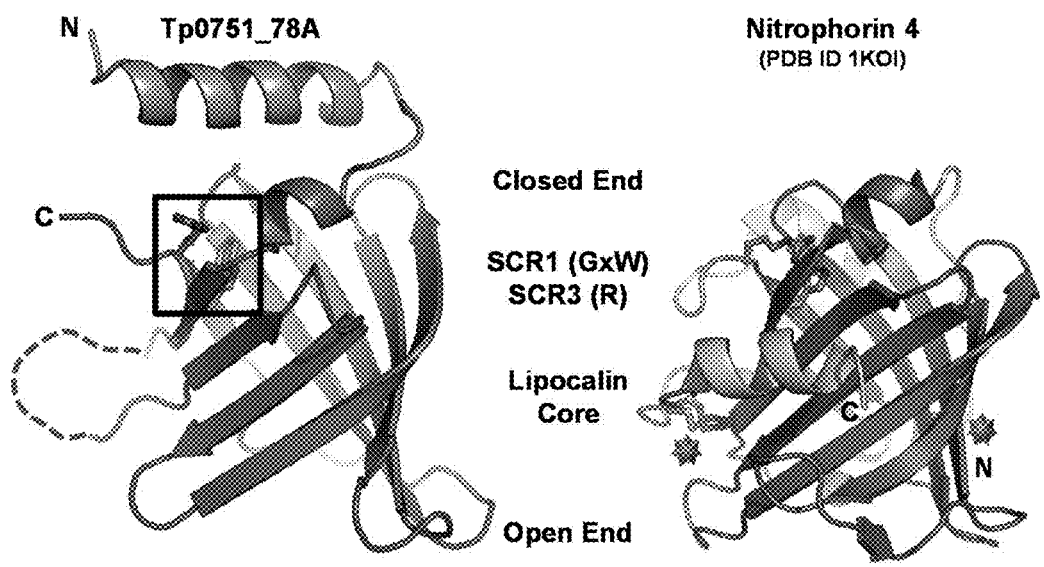
FIGS. 5A-5C. The structural domain of Tp0751 is an outlier lipocalin that lacks a readily accessible ligand binding cleft.

In some examples, such a Tp0751 fragment includes an immune stimulating adjuvant-like sequence. The lipocalin structure lends itself to molecular engineering, especially within the loop regions (e.g., see Skerra (2000) *Biochim. Biophys. Acta*, 1482(1-2):337-350; Skerra (2001) *J. Biotechnol.* 74(4):257-275; Skerra et al. (2008) *FEBS* 11:2677-2683, and US 20060058510, DE19742706A1, DE19742706B4, DE59805995D1, DE59814481D1, EP1017814A1, EP1017814B1, EP1270725A1, EP1270725B1, U.S. Pat. No. 7,250,297, U.S. Pat. No. 7,723,476, U.S. Pat. No. 8,158,753, U.S. Pat. No. 8,536,307, US20100285564, US20120244596, WO1999016873A1). The loop regions of Tp0751 are shown in FIG. 5A. Examples of immune stimulating adjuvant-like sequences include toll-like receptor agonists, as well as agents that can generate a delayed hypersensitivity in the subject (e.g., see Coffman et al. (2010) *Immunity* 33: 492-503; Tomai et al. (2012) Innovation in Vaccinology, Chapter 9 TLR Agonists as Vaccine Adjuvants; Kastenmuller et al. Nature Reviews Immunology (2014) 14:705-711; Bhardwaj et al. (2010) Cancer J. 16(4):382-391; Huleatt et al. (2007) Vaccine 25(4):763-775; Zom et al. (2012) *Advances in Immunology* 114:177-201, all herein incorporated by reference).

Nucleic Acid Molecules

Also provided are isolated nucleic acid molecules that encode Tp0751 protein fragments, such as nucleotides 70-711 or 73-711 of SEQ ID NO: 1, which encode SEQ ID NOS: 7 and 3, respectively, as well as SEQ ID NOS: 14, 17, and 20, which encode SEQ ID NOS: 15, 17, and 19, respectively. In some example, such sequences further include a tag coding sequence at the 3'- or 5'-end. One skilled in the art will recognize that coding sequences for SEQ ID NOS: 4-6 and 8-10, and other TP0751 fragments provided herein, can be readily determined using the genetic code and routine methods. Examples of isolated nucleic acid molecules include cDNA and mRNA.

One skilled in the art will recognize that such sequences can be altered using routine methods in the art (such as recombinant molecular biology methods), while still encoding a Tp0751 protein fragment that retains the ability to function as an immunogen using the disclosed methods. Thus, the present disclosure provides variants of the disclosed Tp0751 nucleic acid sequences, such as a Tp0751 nucleic acid sequence having at least 60%, at least 70%, at least 80%, at least 90%, at least 95%, at least 98%, or at least 99% sequence identity to SEQ ID NO: 14, 17, or 20 or nucleotides 70-711 or 73-711 SEQ ID NO: 1.

For example, the sequence shown in SEQ ID NO: 14, 17, or 20 or nucleotides 70-711 or 73-711 of SEQ ID NO: 1 can be modified by making one or more nucleotide substitutions, which in some examples will not change the encoded peptide sequence due to the degeneracy of the code (e.g., silent mutation), and in other examples will change the sequence of the encoded peptide. Therefore, SEQ ID NO: 14, 17, or 20 or nucleotides 70-711 or 73-711 of SEQ ID NO: 1 can be modified to result in 1 to 20, 1 to 15, 1 to 12, 1 to 10, or 1 to 5 conservative amino acid substitutions, such as 1, 2, 3, 4, 5, 6, 7, 8, 9, 10, 11, 12, 13, 14, 15, 16, 17, 18, 19, or 20 conservative amino acid substitutions, while retaining the ability to encode a Tp0751 peptide fragment that retains the ability to function as an immunogen using the disclosed methods.

In one example, a Tp0453 nucleic acid sequence having at least 60%, at least 70%, at least 80%, at least 90%, at least 95%, at least 98%, or at least 99% sequence identity to SEQ ID NO: 14, 17, or 20 or nucleotides 70-711 or 73-711 of SEQ ID NO: 1, can encode a Tp0751 peptide fragment having at least 60%, at least 70%, at least 80%, at least 90%, at least 95%, at least 98%, or at least 99% sequence identity to any of SEQ ID NOs: 3-10, 15, 16, 18, 19, or 21, while retaining the ability to encode a Tp0751 peptide fragment that retains the ability to function as an immunogen using the disclosed methods.

In some examples, a nucleic acid encoding a variant non-native Tp0751 protein fragment has a coding sequence that retains a mutated HEXXH (SEQ ID NO: 45) site, such as H174A of SEQ ID NO: 4, E175A of SEQ ID NO: 5, H178A of SEQ ID NO: 6, H175A of SEQ ID NO: 8, E176A of SEQ ID NO: 9, H179A of SEQ ID NO: 10, amino acids 174-178 of SEQ ID NO: 4, amino acids 174-178 of SEQ ID NO: 5, amino acids 174-178 of SEQ ID NO: 6, amino acids 175-179 of SEQ ID NO: 8, amino acids 175-179 of SEQ ID NO: 9, and/or amino acids 175-179 of SEQ ID NO: 10 (that is, these coding sequences would not be changed in the variant peptide, unless the change was a silent mutation).

In some examples, a nucleic acid encoding a variant non-native Tp0751 protein fragment has a coding sequence that changes amino acids 121, 122, and/or 125 of SEQ ID NO: 15 or 16, amino acids 100, 101, and/or 104 of SEQ ID NO: 18 or 19, or amino acids 184, 85, and/or 88 of SEQ ID NO: 21, (for example to encode an alanine at these positions).

In addition, SEQ ID NO: 14, 17, or 20 or nucleotides 70-711 or 73-711 of SEQ ID NO: 1 can be modified by making one or more nucleotide (nt) changes without changing the length of the nucleic acid. Therefore, SEQ ID NO: 14, 17, or 20 or nucleotides 70-711 or 73-711 of SEQ ID NO: 1 can be modified by making 1 to 100, 1 to 50, 1 to 20, 1 to 15, 1 to 12, 1 to 10, or 1 to 5 nt substitutions, such as 1, 2, 3, 4, 5, 6, 7, 8, 9, 10, 11, 12, 13, 14, 15, 16, 17, 18, 19, 20, 30, 40, 50, 60 70, 80, 90, or 100 nt substitutions, while retaining the ability to encode a Tp0751 peptide fragment that retains the ability to function as an immunogen using the disclosed methods.

Vectors that include a nucleic acid that encodes a Tp0751 protein fragment (such as any of SEQ ID NOs: 3-10, 15, 16, 18, 19, or 21) are also provided. In one example, the vector is pDEST17 or pET28a. Thus, provided is a pDEST17 vector or a pET28a vector and nucleotides 70-711 or 73-711 of SEQ ID NO: 1.

Also provided are cells that include the vectors and a Tp0751 protein fragment coding sequences (such as SEQ ID NO: 14, 17, or 20 or nucleotides 70-711 or 73-711 of SEQ ID NO: 1). In one example the cell is a prokaryotic cell, such as *E. coli*. Other exemplary cells include insect and yeast cells.

Compositions

Pharmaceutical compositions, which include one or more isolated Tp0751 protein fragments, isolated nucleic acid molecules that encode Tp0751 protein fragments, such as a Tp0751 peptide fragment having at least 60%, at least 70%, at least 80%, at least 90%, at least 95%, at least 98%, or at least 99% sequence identity to any of SEQ ID NOs: 3-10, 15, 16, 18, 19, or 21 or a coding sequence thereof, or vectors that include the nucleic acid, are provided. For example, such a composition can include a pharmaceutically acceptable carrier, such as water, oil, a water and oil emulsion, or saline.

Vaccines, which include one or more isolated Tp0751 protein fragments, isolated nucleic acid molecules that encode Tp0751 protein fragments, or vectors that include the nucleic acid, are provided. For example, such a vaccine composition can include an adjuvant, such as TiterMax Gold (Sigma). In some examples, vaccines include a pharmaceutically acceptable carrier, such as water, oil, a water and oil emulsion, or saline.

Generation of Immune Response Using Tp0751 Fragments

The native and non-native Tp0751 protein fragments disclosed herein (such as those having at least 60%, at least 70%, at least 80%, at least 90%, at least 95%, at least 98%, or at least 99% sequence identity to any of SEQ ID NOs: 3-10, 15, 16, 18, 19, or 21, which in some examples retain or include a mutated binding site), nucleic acids encoding the proteins, or host cells including these nucleic acids can be used to generate an immune response in a subject, such as, but not limited to, a Tp0751-specific CD4+ T cell response, a Tp0751-CD8+ T cell response, a humoral (antibody) response, or combinations thereof. The subject can be a mammal, such as a human, that is at risk for *T. pallidum* infection. The methods include administering to a subject a therapeutically effective amount of one or more of the native or non-native Tp0751 fragments disclosed herein, nucleic acids encoding these proteins, host cells, such as *Listeria* or *Salmonella* host cells, dendritic cells presenting epitopes of the Tp0751 protein fragment, and/or vectors including these nucleic acids, in order to generate an immune response. Thus, a therapeutic composition (such as a vaccine) can include a native or non-native Tp0751 protein fragment, a nucleic acid encoding a such a protein, a vector including the nucleic acid, or a host cell expressing the Tp0751 protein fragment. These compositions can be used in combination. The methods can include selecting a subject in need of treatment, such as a subject at risk for *T. pallidum* infection, such as a subject who is or may become sexually active.

In exemplary applications, compositions are administered to a subject in an amount sufficient to raise an immune response to Tp0751-expressing cells, such as a B cell response. Administration induces a sufficient immune response to protect the subject from subsequent *T. pallidum* infection. Such protection need not be 100%.

For example, such a sufficient immune response can include one that (1) reduces or eliminates chancre formation, such as reduces the volume of a chancre by at least 20%, at least 40%, at least 50%, at least 60%, at least 70%, at least 80%, or at least 90%, at least 100%, such as at least 1.5 fold or at least 2-fold, such as at least 10 days or at least 14 days following subsequent *T. pallidum* infection (for example relative to no Tp0751 fragment administration); (2) reduces the % of chancres that are ulcerated, such as reduces the % ulceration of a chancres by at least 20%, at least 40%, at least 50%, at least 60%, at least 70%, at least 80%, or at least 90%, at least 100%, such as at least 1.5 fold, at least 2-fold, at least 3-fold, at least 4-fold, or at least 5-fold, such as at least 10 days or at least 14 days following subsequent *T. pallidum* infection (for example relative to no Tp0751 fragment administration); (3) reduces the % of darkfield positive lesions (i.e., treponemes present), such as reduces the % of treponemes or darkfield positive lesions by at least 20%, at least 40%, at least 50%, at least 60%, at least 70%, at least 80%, or at least 90%, at least 100%, such as at least 1.5 fold, at least 2-fold, at least 3-fold, at least 4-fold, or at least 5-fold, such as at least 10 days or at least 14 days following subsequent *T. pallidum* infection (for example relative to no Tp0751 fragment administration); (4) reduces *T. pallidum* infection disseminated to lymph nodes (such as popliteal lymph nodes) following subsequent *T. pallidum* infection, such as reduces the *T. pallidum* infection in lymph nodes and other organs and tissues (such as popliteal lymph nodes) by at least 20%, at least 40%, at least 50%, at least 60%, at least 70%, at least 80%, or at least 90%, at least 100%, such as at least 1.5 fold, at least 2-fold, at least 3-fold, at least 4-fold, or at least 5-fold, such as at least 100 days or at least 180 days following subsequent *T. pallidum* infection (for example relative to no Tp0751 fragment administration); (5) reduces orchitis following subsequent *T. pallidum* infection, such as reduces orchitis by at least 20%, at least 40%, at least 50%, at least 60%, at least 70%, at least 80%, or at least 90%, at least 100%, such as at least 10 days or at least 30 days following subsequent *T. pallidum* infection (for example relative to no Tp0751 fragment administration); (6) reduces seroconversion following subsequent *T. pallidum* infection, such as reduces seroconversion by at least 20%, at least 40%, at least 50%, at least 60%, at least 70%, at least 80%, or at least 90%, at least 100%, such as at least 60 days or at least 180 days following subsequent *T. pallidum* infection (for example relative to no Tp0751 fragment administration), (7) reduces the number of necrotic lesions following subsequent *T. pallidum* infection, such as reduces necrotic lesions by at least 20%, at least 40%, at least 50%, at least 60%, at least 70%, at least 80%, or at least 90%, at least 100%, such as at least 10 days or at least 30 days following subsequent *T. pallidum* infection (for example relative to no Tp0751 fragment administration) or combinations thereof.

Amounts effective for this use will depend upon the general state of the patient's health, and the robustness of the patient's immune system. In one example, a therapeutically effective amount of the composition is that which provides either subjective relief of a symptom(s) or an objectively identifiable improvement as noted by the clinician or other qualified observer. In one specific, non-limiting example, a pharmaceutical composition for injection (such as sc, iv or im) administration includes about 0.1 µg to 10 mg (such as 0.1 µg to 5 mg, 0.5 µg to 1 mg or 0.5 µg to 50 µg) of immunogenic Tp0751 protein fragment per subject. Dosages from 0.1 up to about 100 mg per subject can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995. In some examples the patient receives two or more doses of the Tp0751 fragment, such as an initial dose, followed by 1, 2, or 3 booster doses. In some examples, the patient receives no more than 3 doses of the Tp0751 fragment over no longer than a 1 year timeframe.

In some examples, to monitor the antibody response of subjects administered the Tp0751 fragments of the disclosure, antibody levels may be determined. In some instances it will be sufficient to assess the antibody titer in serum or plasma obtained from such a subject. Decisions as to whether to administer booster inoculations or to change the amount of the composition administered to the individual may be at least partially based on the level. The level can be based on routine assays, such as an immunobinding (e.g., ELISA) assay which measures the concentration of antibodies in the serum which bind to a specific antigen, Tp0751.

The ability to neutralize in vitro and in vivo biological effects of the *T. pallidum* can also be assessed to determine the effectiveness of the treatment.

The composition can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995). Thus, the composition can be administered either locally or systemically, such as by intramuscular, subcutaneous, intraperitoneal, intradermal, or intravenous injection, but even oral, nasal, transdermal, vaginal, or anal administration is contemplated. In one embodiment, administration is by subcutaneous or intramuscular injection.

When the Tp0751 protein fragment is administered, to extend the time during which protein is available to stimulate a response, the protein can be provided as an implant, an oily injection, in a liposome, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Adjuvants can also be used in combination with the protein, including, for example, chitosan, aluminum salts, an immunostimulatory oligodeoxynucletoide, liposomes and/or one or more cytokines. The Tp0751 protein fragment can be administered in a liposome.

Optionally, one or more immunostimulatory molecules, such as IL-2, IL-6, IL-12, LFA (for example, LFA-1, LFA-2 and/or LFA-3), CD72, RANTES, G-CSF, GM-CSF, TNF-α, IFN-γ, ICAM-1, B7-1, B7-2, other B7 related molecules, OX-40L and/or or 41 BBL (which can be part of a composition including one or more Tp0751 fragment, such as at least 2 different fragments), or combinations of these molecules, can be used as biological adjuvants (see, for example, Salgaller et al., 1998, *J. Surg. Oncol.* 68(2):122-38; Lotze et al., 2000, *Cancer J Sci. Am.* 6(Suppl 1):S61-6; Cao et al., 1998, Stem Cells 16(Suppl 1):251-60; Kuiper et al., 2000, *Adv. Exp. Med. Biol.* 465:381-90). These molecules can be administered systemically (or locally) to the host. In some examples, IL-2, RANTES, GM-CSF, TNF-α, IFN-γ, G-CSF, LFA-3, CD72, B7-1, B7-2, B7-1 B7-2, OX-40L, 41 BBL and/or ICAM-1 are administered. IL-15 or an IL-15/IL-15 receptor complex can be administered.

A number of means for inducing cellular responses, both in vitro and in vivo, are known. Lipids are capable of assisting in priming T cells in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic Tp0751 fragment. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific T cells when covalently attached to an appropriate peptide or protein (see, Deres et al., *Nature* 342:561, 1989). Further, as the induction of neutralizing antibodies can also be primed with the same molecule conjugated to a protein which displays an appropriate epitope, two compositions can be combined to elicit both humoral and cell-mediated responses where that is deemed desirable.

A pharmaceutical composition, such as a vaccine, including a Tp0751 protein fragment is thus provided. These compositions are used to generate an immune response, such as for immunotherapy.

In one embodiment, the Tp0751 protein fragment is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN40™, TWEEN20™, TWEEN 60™, Zwittergent™ 3-12, TEEPOL HB7™, and SPAN85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). In other embodiments, the Tp0751 fragment is included in a liposome.

Adjuvants can also be administered with the Tp0751 fragment. An adjuvant can be any immunostimulatory molecule, such as a cytokine, immunostimulatory nucleic acid, or a biological adjuvant (see above). The adjuvant can be chitosan. Chitosan is a linear polysaccharide formed from repeating beta (1-4 linked) N-acetyl-D-glucosamine and D-glucosamine units, and is derived from the partial deacetylation of chitin obtained from the shells of crustaceans. Chitosan can be made commercially by a heterogeneous alkaline hydrolysis of chitin to give a product which possesses a random distribution of remaining acetyl moieties. The properties of chitosans depend upon inter alia the degree of deacetylation, and the molecular weight. Most commercially available chitosans contain a population of chitosan molecules of varying molecular weights and varying concentrations of the component N-acetyl-D-glucosamine and D-glucosamine groups. The immunological properties of chitosans are known to be linked to the ratio between the N-acetyl-D-glucosamine and D-glucosamine groups. The efficacy of chitosans as adjuvants depends to a considerable extent on the extent of the level of deacetylation. Thus, in some embodiments, the chitosan is at least 80% deacetylated, see U.S. Pat. No. 6,534,065, which is incorporated herein by reference.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

In another embodiment, the composition includes a nucleic acid encoding a Tp0751 protein fragment. A therapeutically effective amount of the polynucleotide encoding the Tp0751 protein fragment can be administered to a subject in order to generate an immune response. In one specific, non-limiting example, a therapeutically effective amount of the polynucleotide encoding the Tp0751 protein fragment is administered to a subject to treat or prevent the effects of *T. pallidum* infection.

Optionally, a non-pox non-yeast vector is administered that encodes one or more immunostimulatory or costimulatory molecules, such as IL-2, IL-6, IL-12, IL-15, LFA (for example, LFA-1, LFA-2 and/or LFA-3), CD72, RANTES, G-CSF, GM-CSF, TNF-α, IFN-γ, ICAM-1, B7-1, B7-2, other B7 related molecules, OX-40L or 41 BBL, or combinations of these molecules (see, for example, Salgaller et al., 1998, J. Surg. Oncol. 68(2):122-38; Lotze et al., 2000, Cancer J Sci. Am. 6(Suppl 1):S61-6; Cao et al., 1998, Stem Cells 16(Suppl 1):251-60; Kuiper et al., 2000, Adv. Exp. Med. Biol. 465:381-90). In some examples, the vector can encode IL-2, RANTES, GM-CSF, TNF-α, IFN-γ, G-CSF, LFA-3, CD72, B7-1, B7-2, B7-1 B7-2, OX-40L, 41 BBL and/or ICAM-1. In various embodiments, the nucleic acid encoding the biological adjuvant can be cloned into same vector as the Tp0751 fragment coding sequence, or the nucleic acid can be cloned into one or more separate vectors for co-administration. In addition, nonspecific immunomodulating factors such as *Bacillus* Cahnette-Guerin (BCG) and levamisole can be co-administered.

One approach to administration of nucleic acids is direct immunization with plasmid DNA, such as with a mammalian expression plasmid. As described above, the nucleotide sequence encoding a Tp0751 fragment or polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990). In other embodiments, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, for example, U.S. Pat. No. 5,589,466).

In another approach to using nucleic acids for immunization, a Tp0751 fragment can also be expressed by attenuated host cells or non-pox non-yeast viral vectors. These vectors and host cells are disclosed above. Suitable non-pox non-yeast viral vector, include an adenovirus, an alphvirus, a lentivirus, a measles virus or a poliovirus vector. Suitable host cell include an attenuated bacterium, such as *Listeria* or *Salmonella* host cells.

When a non-pox viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant non-pox viral vector, carrying the nucleic acid sequence of a Tp0751 fragment to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of a Tp0751 fragment and a second recombinant viral vector carrying the nucleic acid sequence of one or more costimulatory or immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference). Simultaneous production of an immunostimulatory molecule and the Tp0751 fragment enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, IL-15, interferon, or a nucleic acid encoding these molecules, can be administered in conjunction with a Tp0751 fragment, or a nucleic acid encoding a Tp0751 fragment. The co-expression of a Tp0751 fragment together with at least one immunostimulatory molecule can be effective in an animal model to show immunogenic effects.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to induce an immune response to Tp0751, to treat or ameliorate symptoms or signs of disease, without producing unacceptable toxicity to the subject. Systemic or local administration can be utilized.

Kits Containing Tp0751 Protein Fragments

Isolated Tp0751 protein fragments (e.g., SEQ ID NO: 3 or 7 with a tag, or a protein having at least 60%, at least 70%, at least 80%, at least 90%, at least 95%, at least 98%, or at least 99% sequence identity to any of SEQ ID NO: 3 or 7) or fragments that include a mutated HEXXH (SEQ ID NO: 45) site (e.g., any of SEQ ID NOs: 4-6 or 8-10, or sequences having at least 60%, at least 70%, at least 80%, at least 90%, at least 95%, at least 98%, or at least 99% sequence identity to any of SEQ ID NOs: 4-6 or 8-10 that retain the mutated HEXXH (SEQ ID NO: 45) site) can be part of a kit.

In one example, a kit includes one or more Tp0751 fragments (such as at least 1, at least 2, or at least 10 different fragments, such as 1, 2, 3, 4, or 5 different fragments), such as any of SEQ ID NOS: 3-10, amino acids 79-237 of SEQ ID NO: 2, amino acids 80-237 of SEQ ID NO: 2, amino acids 81-237 of SEQ ID NO: 2, amino acids 82-237 of SEQ ID NO: 2, amino acids 83-237 of SEQ ID NO: 2, amino acids 84-237 of SEQ ID NO: 2, amino acids 85-237 of SEQ ID NO: 2, amino acids 86-237 of SEQ ID NO: 2, amino acids 87-237 of SEQ ID NO: 2, amino acids 88-237 of SEQ ID NO: 2, amino acids 89-237 of SEQ ID NO: 2, amino acids 90-237 of SEQ ID NO: 2, amino acids 91-237 of SEQ ID NO: 2, amino acids 92-237 of SEQ ID NO: 2, amino acids 93-237 of SEQ ID NO: 2, amino acids 94-237 of SEQ ID NO: 2, amino acids 95-237 of SEQ ID NO: 2, amino acids 96-237 of SEQ ID NO: 2, amino acids 97-237 of SEQ ID NO: 2, amino acids 98-237 of SEQ ID NO: 2, amino acids 99-237 of SEQ ID NO: 2, amino acids 100-237 of SEQ ID NO: 2, amino acids 101-237 of SEQ ID NO: 2, amino acids 102-237 of SEQ ID NO: 2, amino acids 103-237 of SEQ ID NO: 2, amino acids 104-237 of SEQ ID NO: 2, amino acids 105-237 of SEQ ID NO: 2, amino acids 106-237 of SEQ ID NO: 2, amino acids 107-237 of SEQ ID NO: 2, amino acids 108-237 of SEQ ID NO: 2, amino acids 109-237 of SEQ ID NO: 2, amino acids 110-237 of SEQ ID NO: 2, amino acids 111-237 of SEQ ID NO: 2, amino acids 112-237 of SEQ ID NO: 2, amino acids 113-237 of SEQ ID NO: 2, amino acids 114-237 of SEQ ID NO: 2, amino acids 115-237 of SEQ ID NO: 2, or a variant having at least 90%, at least 92%, at least 95%, at least 98%, or at least 99% sequence identity to such (such as ones having a mutated HEXXH (SEQ ID NO: 45) site, and/or an E199A mutation (based on the numbering of SEQ ID NO: 2).

Such kits can include one or more Tp0751 protein fragments (or nucleic acid encoding such), for example in a vial or other container, as well as other materials, such as instructions for use in using the agent as an immunogen (e.g., vaccine) against *T. pallidum*. Such kits can also include other agents, such as an adjuvant, syringes, and the like.

EXAMPLE 1

Generation and Purification Tp0751 Fragments

The example describes methods used to generate and purify fragments of Tp0751 (amino acids 54-173, 24-237 and 25-237).

Tp0751 fragments (amino acids 24-237 (SEQ ID NO: 7) or 25-237 (SEQ ID NO: 3)) were separately expressed as a recombinant protein with a 6×His tag using pDEST17 (Life Technologies Gateway system) in *E. coli* B121-AI cells (this results in a 6-His tag at the N-terminus of Tp0751). The cells were grown in LB medium. The Tp0751 protein fragments were induced and expressed while the bacteria were in stationary phase. Briefly, the cells were grown to an OD600 of 1.9 at 37° C., cooled to 16° C. for 1 h, induced with 0.2% L-Arabinose, and grown for 16 h at 16° C. The cells were lysed and the soluble portion of the lysate was purified using affinity chromatography. Briefly, cells were pelleted, protease inhibitor cocktail added, and cells resuspended in 20 mM HEPES/500 mM NaCl/20 mM imidazole/1% glycerol/25 mM CaCl2/10 µM ZnCl2 pH 7.0 before flash freezing. Resuspended cells were stored in −80° C., thawed on ice, and lysed using a detergent (CHAPS) and sonication. The lysate was centrifuged and only the soluble fraction of the lysate was carried forward.

The fractions containing the Tp0751 fragment, as determined by SDS-PAGE, were then purified a second time and buffer exchanged using size exclusion chromatography. Briefly, the lysate was purified using immobilized metal affinity chromatography (IMAC) (on the Akta Prime FPLC fitted with a HisTrap FF (GE) 1 mL column running an imidazole gradient elution. Fractions were pooled and concentrated to 5 mL using a 10,000 Dalton molecular weight cut off centrifugal concentrator. The Affinity Binding/Wash Buffer was 20 mM HEPES/500 mM NaCl/20 mM imidazole/1% glycerol/25 mM CaCl2/10 µM ZnCl2 pH 7.0 and the Affinity Elution Buffer used was 20 mM HEPES/500 mM NaCl/500 mM imidazole/1% glycerol/25 mM CaCl2/10 µM ZnCl2 pH 7.0. The protein was purified a second time using size exclusion chromatography on the Akta Prime FPLC fitted with a Hiload Superdex 75 16/60 column. Fractions were collected, pooled, flash frozen, and stored at −80° C. The steps from lysis to the final freezing are completed within one day.

Constructs encoding N-terminally truncated forms of Tp0751 (Ser78 to Pro237, Tp0751_78; Val99 to Pro237, Tp0751_99) with an E199A mutation (Houston et al., *PLoS Pathog.* 2012; 8(7):e1002822) (SEQ ID NOS: 16 and 19, respectively) and an N-terminally truncated form of wild-type Tp0751 (Glu115 to Pro237, Tp0751_115; SEQ ID NO: 21) were cloned into a modified pET28a vector with a TEV protease cleavable N-terminal hexa-histidine tag. Both constructs were produced in *E. coli* BL21 and purified from the soluble fraction by Ni-affinity chromatography. Proteins were cleaved with TEV protease, purified further by size exclusion and cation exchange chromatography, and exchanged into a final buffer of 20 mM Hepes pH 8.0, 150 mM NaCl, 1% glycerol, 5 µM zinc chloride. Selenomethionine (SeMet)-labelled Tp0751_78A protein was produced using *E. coli* 834 cells in SeMet media (Molecular Dimensions). The culture was grown at 37° C. to an $A_{600}$ of 1.2, cooled to 16° C. and then induced at an $A_{600}$ of 1.8 with 0.4 mM isopropyl 1-thio-β-D-galactopyranoside. After 18 h of growth at 16° C., the cells were harvested by centrifugation, and the SeMet-labeled protein was purified using the same protocol as for the native protein.

This protocol resulted in a >99% pure, soluble protein. The Size Exclusion Buffer used was 20 mM HEPES/150 mM NaCl/25 mM CaCl2/1% glycerol pH 7.0.

One skilled in the art will appreciate that other buffers can be used, such as:
Affinity binding/resuspension/wash buffer: 20 mM HEPES, 500 mM NaCl, 20 mM imidazole, pH 7.0
Affinity elution buffer: 20 mM HEPES, 500 mM NaCl, 500 mM imidazole, pH 7.0
Size exclusion chromatography buffer: 20 mM HEPES, 150 mM NaCl, pH 7.0

EXAMPLE 2

Use of Tp0751 Fragments as an Immunogen

The example describes methods used to immunize rabbits with fragments of Tp0751 (24-237 (SEQ ID NO: 7) and 25-237 (SEQ ID NO: 3)).

An overview of the methods used to immunize (Example 2) and challenge rabbits (Example 3) is shown in FIG. 1. Briefly, two unimmunized control rabbits and three rabbits that had each received three immunizations with wild-type Tp0751 (SEQ ID NO: 7) (125 µg, 1:1 with TiterMax® Gold adjuvant) were challenged with $10^6$ *T. pallidum* at each of 10 sites. These rabbits (termed the donor rabbits) were euthanized at day 14 post-challenge, the lymph nodes were collected and naïve rabbits were infected with these lymph nodes (these are the recipient rabbits). This is called the rabbit infectivity test (RIT) (Example 4). For an RIT, one naïve recipient rabbit receives lymph nodes from one donor rabbit. If the naïve RIT rabbit becomes infected, it is concluded that the *T. pallidum* disseminated to the lymph nodes in the donor rabbit. The organ and tissue burden of *T. pallidum* in the donor rabbits (both control unimmunized and immunized) was determined using quantitative PCR.

Rabbits (New Zealand White specific pathogen free, Males, 3 months old, 2.5 to 3 kg) were shaved across the shoulders and each injection site was cleansed with rubbing alcohol. Rabbits were immunized with Tp0751 fragment amino acids 24-237 (SEQ ID NO: 7) containing an N-terminal 6-His tag (see Example 1) as follows. A water in oil emulsion was made of 0.52 mg/mL of the Tp0751 antigen in aqueous buffer into TiterMax Gold (Sigma cat #T2684 lot SLBB0432V) adjuvant in a ratio of 1:1 following the manufacturer's instructions. Three rabbits were immunized with four subcutaneous (SC) and two intramuscular (IM) injections of the emulsion. Two SC injections of 0.1 mL were done on each shoulder, total of 4 per rabbit per immunization, avoiding previous injection sites. One IM injection of 0.04 mL was done into each quadriceps muscle, for a total of 2 injections per rabbit per immunization.

Figure 2:
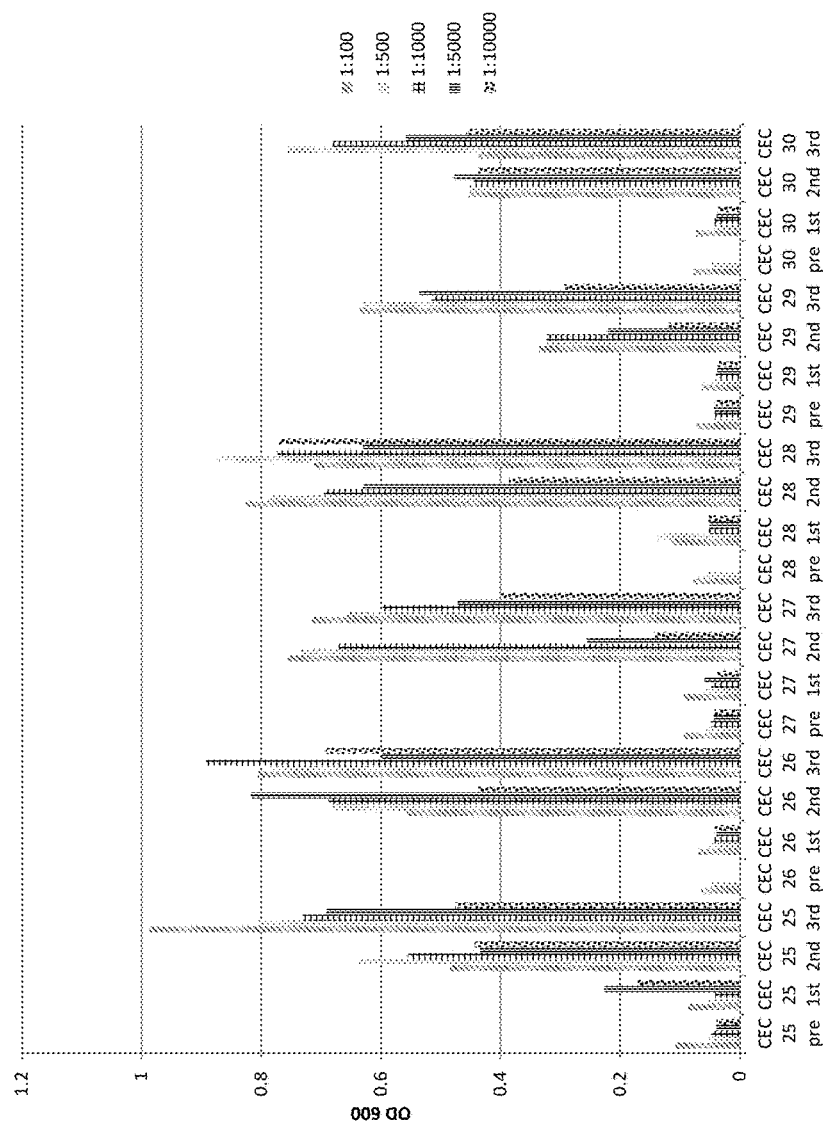
FIG. 2 is a bar graph showing the titers of rabbits immunized with amino acids (aa) 24-237 of Tp0751. The bar graph shows the titers for these 6 different rabbits (#25-30). For each rabbit there are 4 time points. For each time point there are multiple dilutions

One week later the rabbits were bled and titered. Three weeks after the first immunization, the rabbits were boosted, bled, and titered in the same manner. A final boost was done six weeks after the initial immunization. Blood collection was done 7 days after the third immunization. A final blood collection was done 18 days after final immunization (day 67). An intradermal (ID) challenge was performed 25 days after final immunization. FIG. 2 shows the resulting antibody titers (these were determined via ELISA using the recombinant Tp0751 protein and serum collected from the immunized rabbits.). Thus, the Tp0751 fragment aa 24-237 works well as an antigen.

EXAMPLE 3

Tp0751 Fragments Protect Rabbits from Subsequent *T. pallidum* Challenge

The example describes methods used to challenge rabbits with live *T. pallidum* who were previously immunized with fragments of Tp0751 (see Example 2).

Vaccinated rabbits and unvaccinated rabbits were challenged with live *T. pallidum* bacteria to determine how the immunizations affected disease progression and bacterial dissemination. *Treponema pallidum* were propagated using methods known in the art (see Lukehart and Marra. 2007. Isolation and Laboratory Maintenance of *Treponema pallidum*. *Current Protocols in Microbiology*, 12A.1.-12A.1.18 with the exception that testicular extractions were done in an anaerobic environment). The ID challenge was performed as follows. 25 days after the final immunization the backs of rabbits were shaved and cleansed with 70% ethanol and 0.1 mL of $1 \times 10^7$ *Treponema pallidum*/mL in 0.9% saline was intradermally injected, in each of 10 spots. Chancres were monitored and photographed daily for erythema, induration, ulceration, and measured for length, width, and height. Using a syringe fitted with a 26 G needle, the center of the chancres was aspirated, and the aspirate examined using a darkfield microscope.

The immunized rabbits developed lesions upon challenge, as did the control rabbits upon challenge. At the point the rabbits were euthanized (day 14 post-challenge) there were qualitative and quantitative differences between the two groups as shown in Table 2.

TABLE 2

Effect of immunization on chancres following subsequent *T. pallidum* infection

| | % of chancres that are ulcerated | | | average chancre volume (mm³) | |
|---|---|---|---|---|---|
| | Control | Immunized | | Control | Immunized |
| Day 10 | 60 | 10 | Day 10 | 198 | 117 |
| Day 14 | 100 | 57 | Day 14 | 963 | 462 |

Thus, immunization with the Tp0751 fragment partially protects against lesion ulceration and results in smaller chancres. As shown in Table 2 and FIGS. 3A-3B, the immunized rabbits had delayed lesion development compared to the control unimmunized rabbits. All three immunized rabbits had approximately equal, high titers to Tp0751. Ulceration has a very crusty quality and is marked by a brick red color. An ulcerated lesion has a crater-like morphology (raised edge with dipped center). 100% of the lesions in the control rabbits ulcerated compared to about 50% of the lesions in the immunized rabbits (FIG. 3A). 72% of the control rabbit lesions were darkfield positive (i.e., had treponemes present) at day 10 post-challenge compared to 13% of the immunized rabbit lesions. For the darkfield positive lesions from the control rabbits, there were a large number of motile treponemes present, while for the darkfield positive lesions from the immunized rabbits there were only a couple of treponemes present in 10 fields and they were non-motile. In addition, rabbits challenged ID with *Treponema pallidum* had VDRL (Venereal Disease Research Laboratory) seroconversion by day 15, indicating all rabbits had robust infection.

EXAMPLE 4

Rabbit Infectivity Test (RIT)

This example describes the RIT, to determine if *T. pallidum* infection disseminated to lymph nodes in immunized rabbits upon subsequent challenge with virulent *T. pallidum*.

The RIT experiment was performed as follows. Popliteal lymph nodes were removed from ID challenge rabbits, extracted in saline, and injected into the testes of naive rabbits according to Lukehart and Marra (*Current Protocols in Microbiology*, 12A.1.-12A.1.18, 2007). RIT rabbits were monitored by serology (VDRL and FTA-Abs) and palpation of the testes to check for infection. Testicular aspirates were also taken to confirm infection. Thus, as serological markers of infection the VDRL (test for non-treponemal antibodies) and FTA-Abs (test for treponemal antibodies) were used. Physical signs of infection were monitored by looking for orchitis (swelling of the testes due to infection) and by darkfield microscopy (visualization of testicular aspirates).

A summary is provided in Table 3.

TABLE 3

Results of RIT

| | Control lymph node donor | | Immunized lymph node donor | |
|---|---|---|---|---|
| | Day | | Day | |
| Seroconversion | 31 | 100% full seroconversion | 73 | ⅓ rabbits seroconversion |
| | | | 185 | ⅔ rabbit NO seroconversion |
| Orchitis | 37 | 100% had orchitis | 185 | no rabbits developed orchitis |
| Darkfield | 42 | 100% darkfield positive | 134 | darkfield test not done |
| | | | 185 | 2/3 rabbits NO visible bacteria |

The recipient RIT rabbits receiving lymph nodes from the control unimmunized donor rabbits developed orchitis (swelling of the testes associated with *T. pallidum* infection) at day 37 post transfer. These rabbits were euthanized on day 39 (rabbit number 48) and day 42 (rabbit number 47) post transfer. Darkfield analysis of testes aspirates on day 38 post-transfer showed both rabbits had visible treponemes. Table 4 shows the seroconversion status of recipient RIT rabbits from control unimmunized donor rabbits.

TABLE 4

| Donor rabbit | RIT recipient Rabbit # | Pre Bleed | Day 17 | Day 31 | Terminal Bleed |
|---|---|---|---|---|---|
| Control | 47 | no | no | yes | Terminal bleed day 42 yes |
| Control | 48 | no | no | yes | Terminal bleed day 39 yes |

The recipient RIT rabbits receiving lymph nodes from the immunized donor rabbits did not develop orchitis. One of three of these animals seroconverted (rabbit#43). This rabbit never developed orchitis. Rabbit 43 was euthanized on day 134 due to an unrelated suspected gastrointestinal problem (possibly due to eating too many treats). Table 5 shows the seroconversion status of recipient RIT rabbits from immunized donor rabbits.

TABLE 5

| Donor rabbit | RIT Rabbit # | Pre Bleed | Day 17 | Day 31 | Day 51 | Day 73 | Day 106 | Day 147 | Day 175 | Day 185 end study |
|---|---|---|---|---|---|---|---|---|---|---|
| Immunized | 39 | no | no | no | no | no | no | no | no | no |
| Immunized | 42 | no | no | no | no | no | no | no | no | no |

TABLE 5-continued

| Donor rabbit | RIT Rabbit # | Pre Bleed | Day 17 | Day 31 | Day 51 | Day 73 | Day 106 | Day 147 | Day 175 | Day 185 end study |
|---|---|---|---|---|---|---|---|---|---|---|
| Immunized | 43 | no | no | no | yes | yes | yes | euthanized rabbit for unrelated health issues day 134 | | |

In summary, Tp0751 immunization inhibits treponemal dissemination to lymph nodes in rabbits upon subsequent challenge with virulent *T. pallidum*. 2/3 of RIT recipient rabbits that received lymph nodes from Tp0751-immunized donor rabbits show no signs of infection through the 185 days of the experiment (no seroconversion, no orchitis, darkfield negative). This shows *T. pallidum* had not disseminated to the lymph nodes in these two immunized animals. In addition, 2/2 RIT recipient rabbits that received lymph nodes from unimmunized control donor rabbits developed infection by day 17 post-transfer (both rabbits seroconverted by day 17 post-transfer, developed robust orchitis at day 37, and were darkfield positive at the time of euthanasia on days 39 and 42).

EXAMPLE 5

Tp0751 Inactive Fragment has No Effects

The example describes methods used to assess the effects of a Tp0751 fragment with an inactive HEXXH (SEQ ID NO: 45) site in vivo.

Proteolytically active Tp0751 (Example 1, SEQ ID NO: 7), but not an inactive form (SEQ ID NO: 8), caused a reaction in a dose dependent manner.

Injection of 25 μg of wild type Tp0751 (aa 24-237, SEQ ID NO: 7) into rabbits (n=2) in the absence of adjuvant caused a "chancre" to appear at the injection site at day 2 post-injection that disappeared by day 9. To avoid this undesired consequence, the Tp0751 fragment was mutated at its HEXXH (SEQ ID NO: 45) site to AEXXH. In contrast, 25 μg of the proteolytically inactive mutant of Tp0751 (SEQ ID NO: 8) had no reaction.

Similarly, rabbits injected with 25 μg of wild type Tp0751 (aa 24-237, SEQ ID NO: 7)+ TiterMax Gold adjuvant, but not 25 μg of the proteolytically inactive mutant of Tp0751 (SEQ ID NO: 8)+ TiterMax® Gold adjuvant, or TiterMax® Gold adjuvant alone, had ulcerated lesions by day 5 that were similar in gross appearance to chancres arising in rabbits intradermally challenged with $10^6$ *T. pallidum* (day 14 post-challenge).

Thus Tp0751 fragments can be mutated to inactive their HEXXH (SEQ ID NO: 45) site to reduce the appearance of a chancre-like lesion at the injection site.

EXAMPLE 6

Generation and Purification Tp0751 Fragments with Mutated Activation Site

The example describes methods used to generate and purify fragments of Tp0751 (amino acids 24-237 and 25-237) containing a mutated activation site, such as those shown in SEQ ID NOS: 4-6 and 8-10. Such proteins can include a 6×-His tag.

SEQ ID NOS: 4-6 and 8-10 with the HEXXH (SEQ ID NO: 45) site mutated were generated using site-directed mutagenesis. The proteins were purified as described in Example 1.

EXAMPLE 7

Crystallization and Data Collection

Crystals of Tp0751_78A (SEQ ID NO: 16) were originally identified in the SaltRx screen (Hampton Research) using sitting drops at 18° C. The final, refined drops consisted of 0.8 μL Tp0751_78A at 15 mg/mL with 0.8 μL of reservoir solution (0.1 M sodium acetate pH 5.4, 1.6 M sodium formate) and were equilibrated against 120 μL of reservoir solution. Crystals appeared within 5 days and grew to a final size within 3 weeks. For crystallization of SeMet-derivatized protein, 1.0 μL of Tp0751_78A-SeMet at 15 mg/mL was mixed with 1.0 μL of reservoir solution (0.1 M sodium acetate pH 3.6, 1.6 M sodium formate) and equilibrated against 120 μL of reservoir solution. Crystals were cryoprotected in paratone and flash cooled in liquid nitrogen. Diffraction data were collected on beamline 08ID-1 at Canadian Light Source using a wavelength of 0.984 Å for the native data, or an optimized wavelength of 0.9794 Å for the f' selenium edge.

EXAMPLE 8

Data Processing, Structure Determination and Refinement

Diffraction data were processed to 2.15 Å (Tp0751_78A) or 2.80 Å (Tp0751_78A-SeMet) resolution using Imosflm (Battye et al., *Acta Crystallogr D Biol Crystallogr.* 67(Pt 4):271-81, 2011) and Scala (Evans, *Acta Crystallogr D Biol Crystallogr.* 62(Pt 1):72-82, 2006) or Aimless (Evans et al., *Acta Crystallogr D Biol Crystallogr.* 69(Pt 7):1204-14, 2013) in the CCP4 suite of programs (Winn et al., *Acta Crystallogr D Biol Crystallogr.* 67(Pt 4):235-42, 2011). The structure of Tp0751_78A-SeMet was solved by Selenium single wavelength anomalous dispersion. A total of six high confidence Se sites were identified using Phenix.hyss, and enabled building and registering of approximately 70% of the backbone using Phenix.autosol followed by Phenix.autobuild (Adams et al., *Acta Crystallogr D Biol Crystallogr.* 66(Pt 2):213-21, 2010).

Native data were twinned; while Phenix.xtriage (Adams et al., *Acta Crystallogr D Biol Crystallogr.* 66(Pt 2):213-21, 2010) and Aimless identified P622 as the lattice point group, Zanuda in CCP4 identified P321 as the most likely space group. The Tp0751_78A native structure was solved by molecular replacement using a single Tp0751_78A chain from the Se-phased model in Phaser (McCoy, *Acta Crystallogr D Biol Crystallogr.* 63(Pt 1):32-41, 2007), which identified P3$_1$21 as the optimal space group. COOT (Emsley et al., *Acta Crystallogr D Biol Crystallogr.* 66(Pt 4):486-501, 2010) was used for model building and selection of solvent atoms, and the model was refined in Phenix.refine (Afonine et al., *Acta Crystallogr D Biol Crystallogr.* 68(Pt 4):352-67, 2012) using a twin fraction of 0.43 and the merohedral twin operator -H, -K, L. The structure of Tp0751_78A has nine copies in the asymmetric unit; each chain overlays on chain A with an rmsd of 0.30 to 0.60 Å over 115 to 127 aligned Cα positions. Chain A was the most completely modeled with the lowest thermal motion parameters and was used for all analyses.

Complete structural validation was performed with Molprobity (Chen et al., *Acta Crystallogr D Biol Crystallogr.* 66(Pt 1): 12-21, 2010), including analysis of the Ramachandran plots, which showed greater than 93% of residues in the most favored conformations. Five percent of reflections were set aside for calculation of R$_{free}$. Data collection and refinement statistics are presented in Table 6.

EXAMPLE 9

The C-Terminal Domain of Tp0751 Adopts a Compact Beta-Barrel

Figure 4A:
FIGS. 4A-4D. The flexible N-terminus of Tp0751 leads into a compact C-terminal beta-barrel.

Analysis of the mature Tp0751 sequence (Cys24 to Pro237) suggested a prolonged region of disorder extending to Pro98, followed by a set of defined secondary structure elements encompassing Val99 to Lys228 (FIG. 4A). Previous analyses indicated that Tp0751 may be proteolyzed by thrombin at residues Arg77-Ser78, indicating that Ser78 to Pro237 is the functional region of the mature Tp0751 (Houston et al., *PLoS Pathog.* 8(7):e1002822, 2012). However, the lack of any significant sequence identity with known domains or structurally characterized proteins limits insight into the functional mechanism of Tp0751.

Figure 4B:
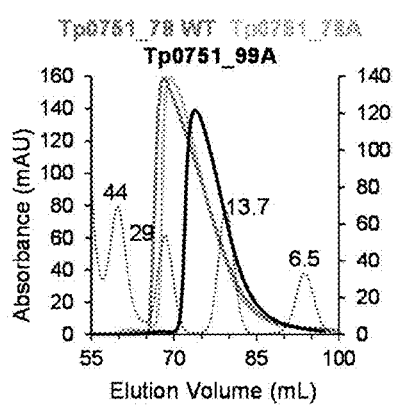

To assess the structure-function relationship of Tp0751, constructs for recombinant protein production that extended from Ser78 or Val99 to the C-terminus (Tp0751_78 (SEQ ID NO: 15) and Tp0751_99 (SEQ ID NO: 18), respectively; FIG. 4A) were generated. Glu199 was mutated to Ala (referred to as Tp0751_78A (SEQ ID NO: 16) and Tp0751_99A (SEQ ID NO: 19), respectively) to stabilize the protein for crystallization studies (Houston et al., *PLoS Pathog.* 8(7):e1002822, 2012). Recombinant proteins produced in *E. coli* were purified, and showed expected elution patterns using size exclusion chromatography, with the similar elution profiles of Tp0751_78 WT and Tp0751_78 E199A (Tp0751_78A) suggesting that the point mutation did not alter protein folding (FIG. 4B).

Figure 4C:
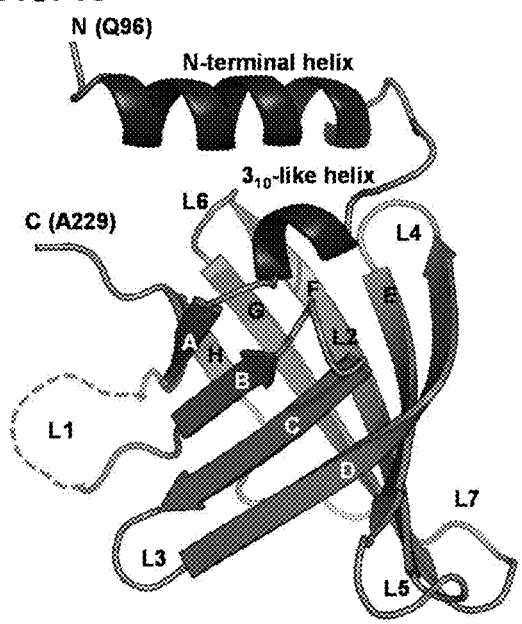

While Tp0751_78 WT was recalcitrant to crystallization, the crystal structure of Tp0751_78A was determined using selenium single wavelength anomalous dispersion (SAD) phasing to a resolution of 2.15 Å (Table 6). The structure of Tp0751_99A was subsequently determined by molecular replacement. Both structures revealed that the C-terminal domain of Tp0751 adopts a compact 8-stranded antiparallel beta-barrel with +1 topology, capped by a short 3$_{10}$-like helix and a longer N-terminal helix (FIG. 4C). Intriguingly, Tp0751 was modeled from Gln96 (Tp0751_78A) or Val199 (Tp0751_99A) to Ala229, suggesting the N-terminal residues of Tp0751_78A (Ser78 to Thr95) were either disordered or proteolyzed in the crystal.

Figure 4D:
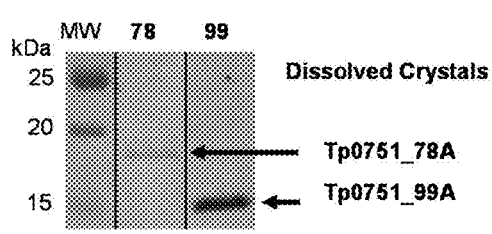

To investigate these two possibilities, crystals of each construct were isolated and analyzed by SDS PAGE. Analysis clearly revealed an intact N-terminal extension present in the Tp0751_78A crystals (FIG. 4D) indicating that N-terminal extension not observed in the crystal structure is due to mobility and not proteolysis. This confirms that the C-terminal region of Tp0751 (Gln96 to Ala229) represents the core structural domain of the protein. In addition, an extended N-terminus on the Tp0751_78A construct is consistent with its marginally expedited elution profile from the size exclusion column compared to the globular protein standards (FIG. 4B).

EXAMPLE 10

Tp0751 Adopts a Non-Canonical Lipocalin Fold

Comparison of the Tp0751_78A structure against the database of known structures using the DALI server revealed a striking similarity to lipocalin domains, specifically Nitrophorins. Tp0751_78A achieved a Z-score of 8.8 (Z<2 is spurious) with the top hit Nitorphorin 4 (PDB ID 1KOI), corresponding to a root mean square deviation of 3.0 Å over 184 aligned positions (FIG. 5A).

TABLE 6

Data collection and refinement statistics.

| | Tp0751_78A-SeMet SAD | Tp0751_78A |
|---|---|---|
| A. Data collection statistics | | |
| Spacegroup | H32 | P3$_1$21 |
| a, b, c (Å) | 146.05, 146.05, 152.82 | 144.72, 144.72, 152.61 |
| α, β, γ (deg.) | 90, 90, 120 | 90, 90, 120 |
| Wavelength | 0.9794 | 0.984 |
| Resolution range (Å) | 65.40-2.80 (2.95-2.80) | 72.36-2.15 (2.19-2.15) |
| Measured reflections | 338,530 (49,052) | 754,198 (36,139) |
| Unique reflections | 15,592 (2,245) | 100,394 (4,902) |
| Redundancy | 21.7 (21.8) | 7.5 (7.4) |
| Completeness (%) | 99.8 (100.0) | 99.9 (100.0) |
| I/σ(I) | 12.5 (2.9) | 10.7 (2.7) |
| R$_{merge}$ | 0.156 (0.966) | 0.122 (0.719) |
| B. Refinement statistics | | |
| Resolution (Å) | | 65.20-2.15 |
| R$_{work}$/R$_{free}$ | | 0.239/0.276 |
| No. of atoms | | |
| Protein (A/B/C/D/E/F/G/H/I) | | 1039/1016/994/1034 1029/1003/950/969/949 |
| Solvent | | 188 |
| Average B-values (Å$^2$) | | |
| Protein (A/B/C/D/E/F/G/H/I) | | 38.3/42.4/38.8/44.2 41.1/45.0/52.1/48.1/51.9 |
| Solvent | | 35.8 |
| r.m.s. deviation from ideality | | |
| Bond lengths (Å) | | 0.003 |
| Bond angles (deg.) | | 0.642 |
| Ramachandran statistics (%) | | |
| Most favoured | | 93.4 |
| Allowed | | 6.6 |
| Disallowed | | 0.0 |

Values in parentheses are for the highest resolution shell

While Tp0751_78A and nitrophorin 4 share only 6% sequence identity, low sequence identity is a common feature of lipocalins (Flower et al., *Biochim Biophys Acta.*

Figure 5B:
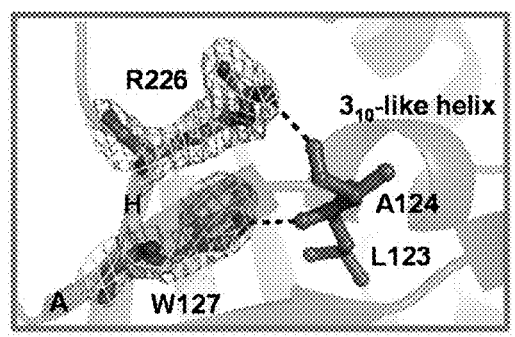

2000; 1482(1-2):9-24; Lakshmi et al., *PLoS One.* 2015; 10(8):e0135507). Lipocalins, along with fatty acid-binding proteins and avidins, are members of the calycin superfamily defined by distinct features of a central beta-barrel and a key structural signature defined by three short conserved regions (SCR1, SCR2, and SCR3). The designation of the Tp0751 structural domain as a lipocalin within the calycin superfamily is confirmed by the eight antiparallel beta-strands with +1 topology that comprise the beta-barrel, combined with the elliptical cross-section and readily distinguishable open and closed ends of the barrel (FIG. 5A). While Tp0751_78A is lacking both N- and C-terminal features common to lipocalins that tend to be pinned to the outside of the beta-barrel by disulfide bonds, these are not requirements for lipocalin classification (FIG. 5A, right). More specifically, Tp0751 contains an outlier lipocalin domain, as opposed to a kernel lipocalin, since it does not possess all three SCRs. This is also the basis for Nitrophorins being classified as outlier lipocalins (Flower et al., *Biochim Biophys Acta.* 2000; 1482(1-2):9-24). SCR1 localizes to the $3_{10}$ helix and strand A, centered on a GxW motif (Gly125 and Trp127 in Tp0751; FIG. 5B). Although SCR3 is distal in the primary sequence, residing on strand H, the key basic residue (Arg226 in Tp0751) stacks on top of the SCR1 Trp and forms a hydrogen bond to the backbone carbonyl of the preceding coil (FIG. 5B). SCR2, which is localized to Strand F-Loop 6-Strand G, is not conserved in Tp0751, consistent with other bacterial lipocalins.

Figure 5C:
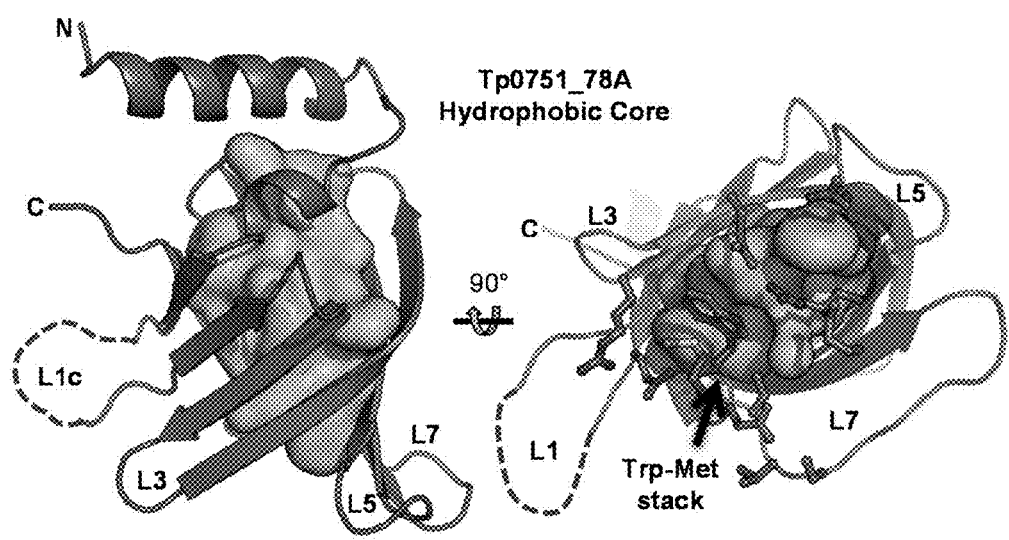

Lipocalins that are closely structurally related tend to have similar functions, however it is highly unlikely that Tp0751 has a function similar to nitrophorins, as the residues required for heme coordination and transport are not conserved. More broadly, a common feature of lipocalins is the presence of a hydrophobic ligand-binding pocket within the beta-barrel (Flower et al., *Biochim Biophys Acta.* 2000; 1482(1-2):9-24; Schiefner et al., *Acc Chem Res.* 2015; 48(4):976-85). This pocket and surrounding loops of the open end (L1, L3, L5, and L7) serve as a cup to coordinate an extensive variety of hydrophobic ligands for transport, catalytic or sequestration purposes. While Loop 1 serves as a lid for the cup-like binding site, Loop 1 of Tp0751_78A is exposed and partially disordered in the structure (FIG. 5C). Despite this, there is still no notable hydrophobic pocket, which is predominately due to Loop 7 that caps the hydrophobic core with a stacked Trp-Met (FIG. 5C, right). While displacement of Loop 7 could expose a potential ligand-binding site, several other polar residues are also found to cap the hydrophobic core (FIG. 5C, right), suggesting that Tp0751 has repurposed the open end of the lipocalin domain for a function other than hydrophobic ligand binding.

EXAMPLE 11

Tp0751 Host ECM Binding Peptides Map to the Lipocalin Domain

To dissect the contributions of individual substructures in mediating attachment to host ECM components, a peptide library was used (Cameron et al., *Infect Immun.* x; 73(11): 7485-94, 2005). Of the 13 native Tp0751 peptides tested, p4 (SEQ ID NO: 25), p6 (SEQ ID NO: 27), and p11 (SEQ ID NO: 32) displayed statistically significant binding to fibrinogen ($p \leq 0.0004$), fibronectin ($p \leq 0.0001$), collagen I ($p \leq 0.0113$), and collagen IV ($p \leq 0.0002$) (FIG. 3A). Peptide p10 (SEQ ID NO: 31) also showed significant binding to fibrinogen (p<0.0001), fibronectin (p<0.0001), and collagen IV (p=0.0006), but not to collagen I (p=0.0653). Neither the scrambled versions of p4 (p4scr, SEQ ID NO: 35) or p6 (p6scr, SEQ ID NO: 36) showed binding suggesting that the interaction is sequence dependent.

Figure 6A:
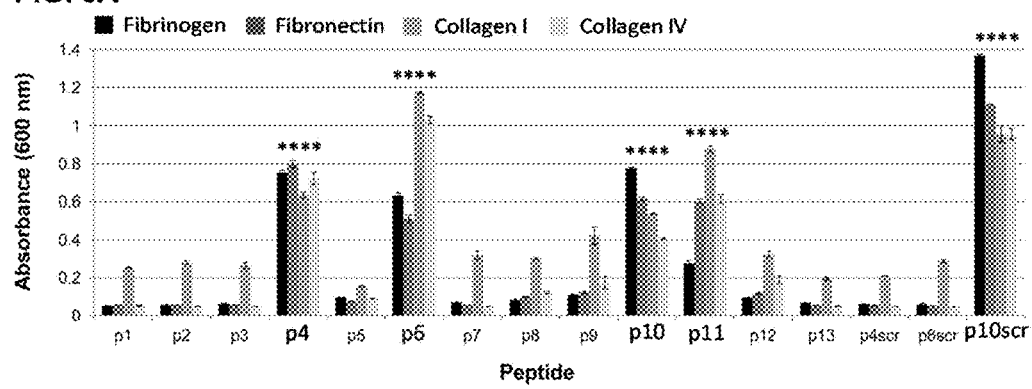

Moreover, the overlapping peptides 3, (SEQ ID NO: 24), 5 (SEQ ID NO: 26) and 7 (SEQ ID NO: 28) exhibited little to no binding, consistent with a key role for the central four amino acids unique to p4 (PVQT) and p6 (LWIQ). Notably, both of these four residue motifs are significantly altered in the scrambled peptides. In contrast to the p4scr and p6scr, p10scr also exhibited statistically significant levels of binding to each of the tested host ECM proteins (FIG. 6A). Analysis of the overlapping regions of p10 and p11 (FIG. 6B) revealed an arginine triplet framed by hydrophobic residues. Consistent with the observation of an influential role for basic residues, it has been shown that the FbsA adhesin from *Streptococcus agalactiae* binds fibrinogen via a 16-amino acid motif containing R-R-X-R/K (SEQ ID NO: 42) and X-X-R/K-X-X (SEQ ID NO: 43) sequences (Schubert et al., *Mol Microbiol.* 2002; 46(2):557-69). Studies using site-directed mutagenesis and synthetic peptides have also shown positively charged residues to be important in mediating binding of different MSCRAMMs (Microbial Surface Components Recognizing Adhesive Matrix Molecules) to fibrinogen and fibronectin (Deivanayagam et al., *EMBO J.* 2002; 21(24):6660-72; Keane et al., *Mol Microbiol.* 2007; 63(3):711-23; Konkel et al., *Mol Microbiol.* 1997; 24(5):953-63). Furthermore, both arginine and lysine residues have been shown to comprise part of a fibronectin binding motif in BBK32, a host ECM-interacting protein from the related pathogenic spirochete, *Borrelia burgdorferi* (Prabhakaran et al., *PLoS One.* 2009; 4(4):e5412).

Figure 6B:
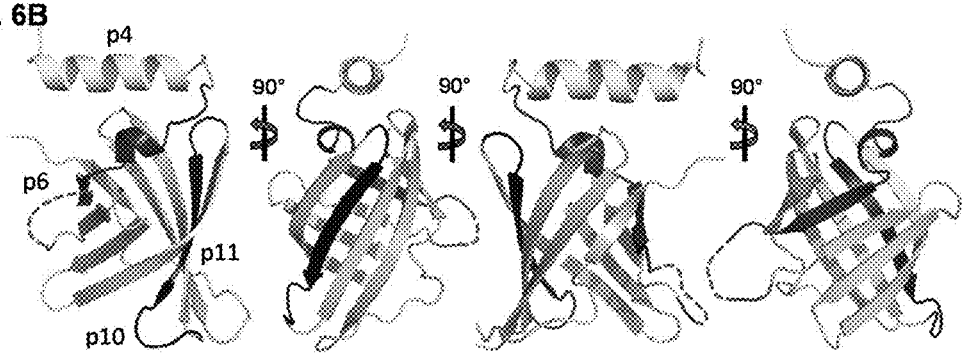

To establish the spatial relationship between the peptides with respect to the intact Tp0751, each of the peptides that showed ECM binding was mapped onto the Tp0751 structure. Notably, all positive peptides are contained within the lipocalin domain highlighting the importance of this ordered region of the protein for interfacing with the host (FIG. 6B). Peptide 4 maps to the highly ordered N-terminal helix while p6 incorporates a $3_{10}$-like helix and a short strand (strand A labeled in FIG. 4C)) and p10 and p11 map to strands E/F and F/G, respectively. In the context of the Tp0751 crystal structure, the central portion of peptide 10 forms a strand in an extended beta sheet. Of the three arginine residues, the peripheral two are directed outwards while the central residue is directed into the core of the lipocalin fold. The p10 scrambled peptide largely mimics this spatial separation of the arginine residues (RxRxxR; SEQ ID NO: 44) (FIG. 6C) and may explain the enhanced binding observed relative to the native peptide.

EXAMPLE 12

Tp0751 Peptides 4, 6, 10, and 11 Bind Host Proteins

The ability of 13 overlapping Tp0751 synthetic 24-mer peptides (p1-p13; SEQ ID NOS: 22-34, respectively, 2.0 µg per well) and scrambled versions of peptides 4 (p4scr; SEQ ID NO: 35), 6 (p6scr; SEQ ID NO: 36) and 10 (p1oscr; SEQ ID NO: 37) (2.0 µg per well each) to bind immobilized fibrinogen, fibronectin, collagen type I, and collagen type IV (0.5 µg per well each) was assessed using 96-well plate binding assays (FIG. 6A).

For these bind assays, thirteen overlapping 24-mer peptides (p1-p13) that spanned the Tp0751 amino acid sequence from residue $T^{46}$-$P^{237}$ were synthesized as previously described (Cameron et al., *Infect Immun.* 2005; 73(11):7485-

94). Each synthetic peptide shared 10 overlapping amino acids with neighboring upstream and downstream peptides. Scrambled versions of peptides 4 (p4scr), 6 (p6scr), and 10 (p10scr) were also prepared. All 16 synthetic peptides contained N-terminal six-histidine tags to allow for detection. Plasminogen-depleted human fibrinogen (Calbiochem) was from VWR International. Laminin isolated from Engelbreth-Holm-Swarm murine sarcoma basement membrane and fibronectin isolated from human plasma were purchased from Sigma-Aldrich Canada Ltd. (Oakville, ON). Human collagen types I and IV (Rockland Immunochemicals, Inc.) were from VWR International.

To test for binding of synthetic Tp0751 peptides p1-p13, p1scr, p6scr, and p10scr to the host proteins fibrinogen, fibronectin, laminin, collagen type I, and collagen type IV, binding assays were performed as previously described (Cameron, *Infect Immun.* 2003; 71(5):2525-33; Cameron et al., *Infect Immun.* 2005; 73(11):7485-94). Plates were read at 600 nm with a BioTek enzyme-linked immunosorbent assay plate reader (Fisher Scientific, Ottawa, ON). Average absorbance readings (600 nm) from three wells are presented with bars indicating standard error. For statistical analyses, attachment of each host-binding Tp0751 peptide (p4, p6, p10, p11, and p10scr) to each host protein was compared to the levels of binding exhibited by peptides p1, p2, p3, p5, p7, p8, p9, p12, p13, p4scr, and p6scr, using the Student's two-tailed t test.

As shown in FIG. 6A, Tp0751 peptides p4, p6, p11, and p10scr exhibited statistically significant levels of binding to all four host proteins (*$p \leq 0.0113$). Peptide p10 showed significant binding to fibrinogen, fibronectin, and collagen IV ($p \leq 0.0006$) but not to collagen I. Peptides p4, p6, p10 and p11 are mapped onto the Tp0751 lipocalin domain (FIG. 6B) and the sequences of peptides p4, p6, p10 and p11 are shown in FIG. 6C. The box highlights the overlapping sequences of p10 and −11 (FIG. 6C). The central portion of p10 scrambled is shown in brackets to highlight the spacing of the arginine residues.

EXAMPLE 13

The Host ECM Binding Peptide p10 Prevents Bacterial Adhesion to Host Cells

Figure 7:
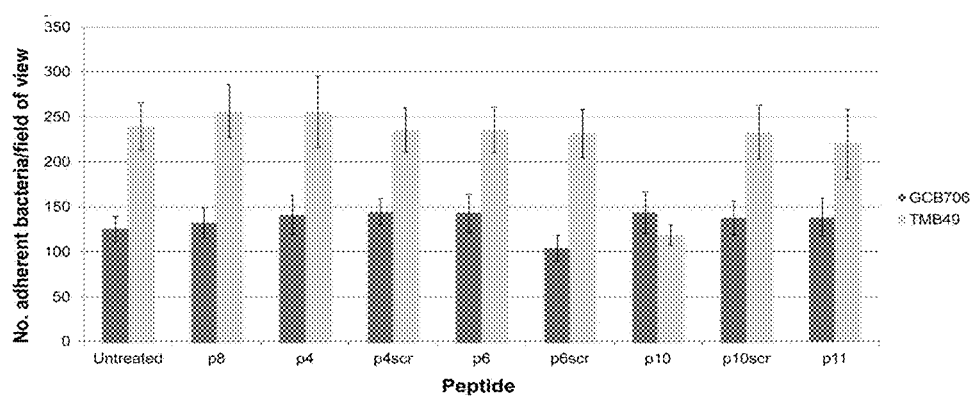
FIG. 7 is a bar graph showing that Tp0751 peptide 10 (SEQ ID NO: 31) inhibits adhesion of Tp0751-expressing *B. burgdorferi* to HUVEC monolayers.

To investigate the possibility that the Tp0751 ECM binding peptides could modulate adhesion to host cells, we first needed to overcome the recalcitrance of *T. pallidum* to in vitro culturing and genetic manipulation. To accomplish this, the related spirochete, *Borrelia burgdorferi* was engineered to heterologously express Tp0751 (strain TMB49) and compared its capacity to adhere to HUVEC (Human Umbilical Vein Enothelial Cells) relative to a non-adherent, non-transformed *B. burgdorferi* strain (GCB706) alone or individually preincubated with the Tp0751 synthetic peptides (FIG. 7).

While peptides p4 (SEQ ID NO: 25), p6 (SEQ ID NO: 27), and p11 (SEQ ID NO: 32) did not alter adhesion of the TMB49 strain, incubation with peptide p10 significantly reduced binding of TMB49 to HUVEC monolayers. Also, p10 significantly reduced binding of TMB49 to HUVEC monolayers compared to the binding levels exhibited following preincubation with the scrambled peptide, p10scr. A negative control peptide (p8; SEQ ID NO: 29) that failed to bind the ECM components tested had no effect on HUVEC adherence by either *Borrelia* strain. Peptide p9 (SEQ ID NO: 30) inhibits binding of TMB49 to HUVEC monolayers (data not shown). Peptides p9 and p10 overlap by 10 residues (RKTVSFLTRN; amino acids 15-24 of SEQ ID NO: 30).

These results demonstrate that p10 is capable of competitively inhibiting binding of Tp0751-expressing *B. burgdorferi* to HUVEC monolayers, indicating that this region of Tp0751 may mediate binding to the host endothelium during infection. Interestingly, the scrambled version of peptide 10, which exhibited very high levels of binding to all four host ECM components in the peptide binding assays, failed to inhibit binding of Tp0751-expressing *B. burgdorferi* to HUVEC monolayers. This raises the possibility that adherence of Tp0751 to HUVEC cells is mediated via an interaction involving the p10 region and a host cell receptor that excludes the ECM components analyzed. The finding that peptides p4, p6, and p11 failed to inhibit attachment, together with the peptide binding results, indicates that these regions may not be involved in endothelial cell attachment, but may still be required for attachment to components of the ECM.

EXAMPLE 14

Tp0751 Peptide 10 Inhibits Adhesion of Tp0751-Expressing *B. burgdorferi* to HUVEC Monolayers GFP-expressing *B. burgdorferi* strains GCB706 (non-infectious) and TMB49 (non-infectious, expressing FLAG-tagged Tp0751 with BBK32 signal sequence in trans) were assessed for their ability to adhere to HUVEC monolayers that were preincubated with synthetic Tp0751 peptides (p4, p6, p8, p10, p11, p4scr, p6scr, and p10scr, (SEQ ID NOS: 25, 27, 29. 31. 33, 35, 36 and 37, respectively; 0.1 µg per well) under static conditions.

For the peptide competitive inhibition assay pooled donor human umbilical vein endothelial cells (HUVECs) purchased from Lonza (Allendale, N.J.) were cultured in endothelial growth medium-2 (EGM-2) (Lonza) at 37° C. in an atmosphere of 5% CO2, as per manufacturer's instructions. *Borrelia burgdorferi* strains were cultivated at 36° C. in an atmosphere of 1.5% $CO_2$ in BSK-II medium (Barbour, *Yale J Biol Med.* 57:2525-33, 1984) with appropriate antibiotics (100 µg/mL gentamycin, 200 µg/mL kanamycin).

Stationary adhesion assays were adapted from (Szczepanski et al. (*J Clin Invest.* 85(5):1637-47, 1990) and Cameron et al. (J Bacteriol. 190(7):2565-71, 2008). HUVECs (passage 2-3) were seeded in 4-well chamber slides (Nalge Nunc International, Rochester, N.Y.), coated with 500 µg/mL phenol-red free matrigel (Corning, Tewksbury, Mass.) and grown 20 h at 37° C. in 5% $CO_2$ to form confluent monolayers. Synthetic Tp0751 peptides (p4, p6, p10, p11, p8, p4scr, p6scr, and p10scr) were diluted to 500 µg/mL in HEPES buffered saline solution (Lonza) and HUVECs were pre-incubated with 0.1 µg of Tp0751 peptide per well for 3 h at 37° C. in 5% $CO_2$. Peptide solutions were removed from HUVECs prior to the addition of bacteria. *Borrelia burgdorferi* strains were cultured in biological triplicate, and two days prior to the experiment, *B. burgdorferi* cultures were passaged to 6×10⁵ cells/mL and grown for 48 h to reach a concentration of 2×10⁷ cells/mL. *Borrelia burgdorferi* cultures were then centrifuged and resuspended in a 3:1 mixture of BskII:EGM-2 and 1.4×10⁷ cells of each biological replicate were added to HUVECs in duplicate wells. Chamber slides were incubated for 12 h at 36° C. in 1.5% $CO_2$, washed three times with warm HEPES buffered saline to remove non-adherent bacteria, and fixed in buffered 10% formalin (Fischer Scientific, Ottawa, ON). Quantitation of *B.* burgdorferi adhesion to HUVECs was achieved by counting GFP-expressing bacteria in ten fields of view from duplicate wells for each biological replicate under 400× magnification on a Nikon 80i fluorescence microscope (Meridian Instrument Company, Inc., Kent, Wash.) fitted with a monochrome digital camera, a dark-field condenser, and fluorescein filter (Excelitas Technologies, Mississauga, ON).

Mean counts +/−standard error of the mean from ten fields of view for each biological replicate are presented with bars indicating standard error. For statistical analyses, attachment by strain TMB49 to HUVEC monolayers preincubated with peptides p4, p6, and p10 was compared to the attachment of strain TMB49 in the presence of corresponding scrambled peptides, using the Student's two-tailed t-test. As shown in FIG. 7, strain TMB49 exhibited statistically significant lower levels of binding to HUVEC monolayers preincubated with peptide p10 when compared to the levels of binding when preincubated with the scrambled version of peptide 10 (p10scr).

EXAMPLE 15

The Tp0751 Lipocalin Beta Barrel Structural Domain is Sufficient to Induce Platelet Clot Formation Some invasive bacteria, including pathogenic strains of Staphylococcus aureus, express proteins that promote blood coagulation as a key pathogenic mechanism for establishing host infections (McAdow et al., J Innate Immun 4:141-8. 2012). Previously, it was demonstrated that full-length Tp0751 (Cys24-Pro237) is capable of binding to two host proteins with key roles in clot formation (fibrinogen and fibronectin) (Houston et al., Infect Immun 83:4204-16, 2015), suggesting a role in host blood coagulation modification. To demonstrate that the lipocalin beta barrel domain of Tp0751 is also able to modify the host blood coagulation cascade, platelet clotting assays were performed which compared the ability of Tp0751 and a negative control recombinant protein, Tp0327, to induce blood clots.

Figure 8:
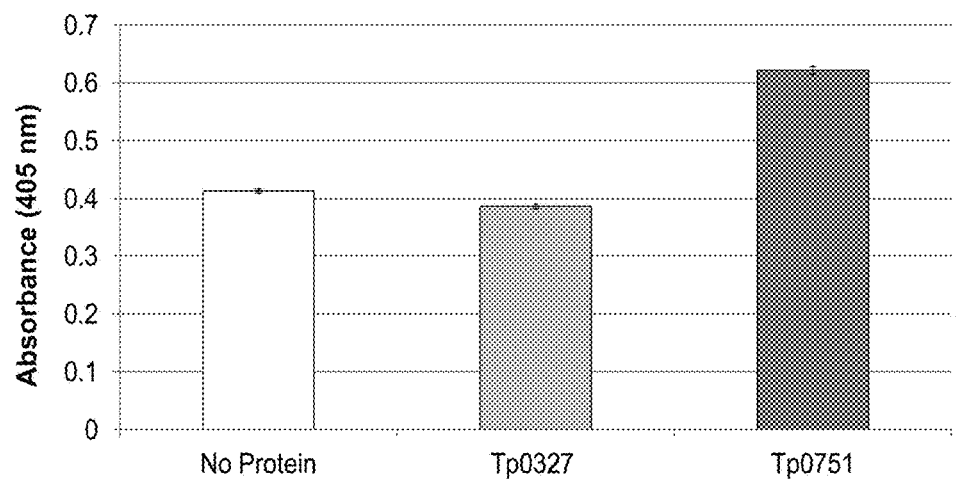
FIG. 8. is a bar graph showing that the Tp0751 lipocalin beta barrel structural domain is sufficient to induce platelet clot formation.

Blood from healthy volunteers was drawn into BD (Franklin Lakes, N.J.) Acid Citrate Dextrose (ACD)-containing vacutainers (supplied by VWR International, Mississauga, ON). Platelet Rich Plasma (PRP) was then separated by centrifugation at 250×g for 10 minutes. Recombinant proteins (Tp0751_E115-P237 and the negative control, Tp0327) were diluted in Saline-Modified Tyrodes Buffer (MTB; 150 mM NaCl; 0.34 mM $Na_2HPO_4$; 2.9 mM KCl; 12 mM $NaHCO_3$; 20 mM Hepes; pH 7.0; 5 mM glucose; 0.35% (w/v) bovine serum albumin) to a final concentration of 30 μM. Sixty two microliltres of the protein solutions were added in quintuplicate to Sarstedt Microtest flat-bottom 96-well plates (Nimbrecht, Germany). Platelet-Rich Plasma (PRP; 38 μl) was then added to each well, mixed gently, and incubated at 37° C. in a BioTek Synergy HT plate reader (Fisher Scientific). Absorbance readings (405 nm) were measured at 5 minute intervals for 140 minutes. An additional negative control consisted of MTB and PRP in the absence of recombinant protein. Statistical analyses were performed using the Student's two-tailed t test. An increase in absorbance correlates to an increase in platelet clot formation (FIG. 8). Average absorbance readings from 5 wells are presented with bars indicating standard error. For statistical analyses, clot formation in the presence of Tp0751_115 was compared to the levels of clot formation in the presence of a negative control protein (Tp0327) and clot formation in the absence of a recombinant protein. Tp0751_115 induced significantly higher levels of clot formation compared to Tp0327 ($p<0.0001$) and wells without recombinant protein ($p<0.0001$).

As shown in FIG. 8, Tp0751_115 (SEQ ID NO: 21) induced a statistically significant increase in platelet clot formation when compared the levels of clot formation induced by the negative control protein Tp0327 ($p<0.0001$) and when no recombinant protein was present ($p<0.0001$). These results demonstrate that the lipocalin beta barrel structural domain of Tp0751 alone is capable of promoting platelet clot formation.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims.

We claim:

1. A vaccine composition comprising:
   a therapeutically effective amount of an isolated Tp0751 protein fragment consisting of SEQ ID NO: 5, and optionally a purification tag; and
   a therapeutically effective amount of an adjuvant.

2. A vaccine composition, comprising:
   a therapeutically effective amount of an isolated Tp0751 protein fragment consisting of the protein sequence of SEQ ID NO: 7, and optionally a purification tag; and
   a therapeutically effective amount of an adjuvant.

3. The vaccine composition of claim 1, further comprising a pharmaceutically acceptable carrier.

4. The vaccine composition of claim 3, wherein the pharmaceutically acceptable carrier comprises saline or phosphate-buffered saline.

5. A method of stimulating an immune response against a Tp0751 protein, comprising:
   administering a therapeutically effective amount of the vaccine composition of claim 1 to a subject.

6. The method of claim 5, wherein the method induces serum antibodies which have neutralizing activity for Tp0751 protein.

7. The method of claim 5, wherein the subject is a mammalian subject.

8. The method of claim 5, wherein the immune response is a B cell response.

9. The vaccine composition of claim 2, further comprising a pharmaceutically acceptable carrier.

10. The vaccine composition of claim 9, wherein the pharmaceutically acceptable carrier comprises saline or phosphate-buffered saline.

11. A method of stimulating an immune response against a Tp0751 protein, comprising:
    administering a therapeutically effective amount of the vaccine composition of claim 2 to a subject.

12. The method of claim 11, wherein the method induces serum antibodies which have neutralizing activity for Tp0751 protein.

13. The method of claim 11, wherein the subject is a mammalian subject.

14. The method of claim 11, wherein the immune response is a B cell response.

15. A method of stimulating an immune response against *Treponema pallidum* in a subject, comprising:
    administering a therapeutically effective amount of the vaccine composition of claim 1 to a subject.

16. The method of claim 15, wherein the subject is human.

17. A method of stimulating an immune response against *Treponema pallidum* in a subject, comprising:
    administering a therapeutically effective amount of the vaccine composition of claim 2 to a subject.

18. The method of claim 17, wherein the subject is human.

* * * * *

UNITED STATES PATENT AND TRADEMARK OFFICE
CERTIFICATE OF CORRECTION

PATENT NO. : 9,913,889 B2
APPLICATION NO. : 14/993961
DATED : March 13, 2018
INVENTOR(S) : Cameron et al.

Page 1 of 1

It is certified that error appears in the above-identified patent and that said Letters Patent is hereby corrected as shown below:

In the Specification

Column 1, Line 14, "This invention was made with government support under AI051334 awarded by the National Institute of Allergy and Infectious Diseases." should read --This invention was made with government support under AI051334 awarded by the National Institutes of Health.--.

Signed and Sealed this
Fourteenth Day of May, 2024

Katherine Kelly Vidal
*Director of the United States Patent and Trademark Office*

SEQUENCE LISTING

```
<160> NUMBER OF SEQ ID NOS: 45

<210> SEQ ID NO 1
<211> LENGTH: 714
<212> TYPE: DNA
<213> ORGANISM: Treponema pallidum
<220> FEATURE:
<221> NAME/KEY: CDS
<222> LOCATION: (1)..(714)

<400> SEQUENCE: 1 gtg aat aga cct tta ctg agt gtg gcc gga tcg ttg ttc gtc gct gcg      48
Val Asn Arg Pro Leu Leu Ser Val Ala Gly Ser Leu Phe Val Ala Ala
1               5                   10                  15 tgg gct cta tat att ttc tcc tgc ttt cag cac ggt cac gtt cct cca      96
Trp Ala Leu Tyr Ile Phe Ser Cys Phe Gln His Gly His Val Pro Pro
            20                  25                  30 cgc aga att ccc ccg cat gat acc ttc ggc gct cta ccc act gct gca     144
Arg Arg Ile Pro Pro His Asp Thr Phe Gly Ala Leu Pro Thr Ala Ala
        35                  40                  45
```

| | | | | | | | | | | | | | | | | |
|---|---|---|---|---|---|---|---|---|---|---|---|---|---|---|---|---|
| ctt | ccc | agc | aac | gcg | cgg | gac | acc | gcc | gca | cac | ccg | tct | gac | acg | gca | 192 |
| Leu | Pro | Ser | Asn | Ala | Arg | Asp | Thr | Ala | Ala | His | Pro | Ser | Asp | Thr | Ala | |
| | | 50 | | | | 55 | | | | 60 | | | | | | |

```
        gac aat acg tcc ggc tcg tcc acc acg aca gac cca cgg tca cat gga      240
        Asp Asn Thr Ser Gly Ser Ser Thr Thr Thr Asp Pro Arg Ser His Gly
        65                  70                  75                  80 aac gcc ccg ccg gcc cct gta ggc gga gca gca cag aca cac aca caa      288
        Asn Ala Pro Pro Ala Pro Val Gly Gly Ala Ala Gln Thr His Thr Gln
                            85                  90                  95 ccg cct gta caa aca gca atg cgc ata gcc ctt tgg aac cgt gca aca      336
        Pro Pro Val Gln Thr Ala Met Arg Ile Ala Leu Trp Asn Arg Ala Thr
                    100                 105                 110 cat ggt gaa cag gga gca ctc cag cac ctc ttg gca gga ctg tgg ata      384
        His Gly Glu Gln Gly Ala Leu Gln His Leu Leu Ala Gly Leu Trp Ile
                115                 120                 125 caa act gaa atc tcc ccg aac tca ggc gat atc cat cct ctg ctg ttt      432
        Gln Thr Glu Ile Ser Pro Asn Ser Gly Asp Ile His Pro Leu Leu Phe
        130                 135                 140 ttt gac cga gaa cac gcg gag atc aca ttc tca cgc gca tca gtc caa      480
        Phe Asp Arg Glu His Ala Glu Ile Thr Phe Ser Arg Ala Ser Val Gln
        145                 150                 155                 160 gaa atc ttc ctg gta gat agc gcg cac aca cac cgc aag acg gtg tca      528
        Glu Ile Phe Leu Val Asp Ser Ala His Thr His Arg Lys Thr Val Ser
                            165                 170                 175 ttt ctc acg cgc aac acc gca att tcc agc atc cgc cgc ctt gag          576
        Phe Leu Thr Arg Asn Thr Ala Ile Ser Ser Ile Arg Arg Leu Glu
                        180                 185                 190 gta aca ttt gaa tcc cac gag gtg ata cac gta agg gcg gtt gaa gac      624
        Val Thr Phe Glu Ser His Glu Val Ile His Val Arg Ala Val Glu Asp
                    195                 200                 205 gta gca cgg ctc aaa att ggc agc acg tcg atg tgg gac ggt caa tac      672
        Val Ala Arg Leu Lys Ile Gly Ser Thr Ser Met Trp Asp Gly Gln Tyr
                210                 215                 220 acc aga tat cac gcc ggt ccg gct agt gct cct tcg ccc tga              714
        Thr Arg Tyr His Ala Gly Pro Ala Ser Ala Pro Ser Pro
        225                 230                 235

<210> SEQ ID NO 2
<211> LENGTH: 237
<212> TYPE: PRT
<213> ORGANISM: Treponema pallidum

<400> SEQUENCE: 2

Val Asn Arg Pro Leu Leu Ser Val Ala Gly Ser Leu Phe Val Ala Ala
1               5                   10                  15

Trp Ala Leu Tyr Ile Phe Ser Cys Phe Gln His Gly His Val Pro Pro
            20                  25                  30

Arg Arg Ile Pro Pro His Asp Thr Phe Gly Ala Leu Pro Thr Ala Ala
        35                  40                  45

Leu Pro Ser Asn Ala Arg Asp Thr Ala His Pro Ser Asp Thr Ala
    50                  55                  60

Asp Asn Thr Ser Gly Ser Ser Thr Thr Thr Asp Pro Arg Ser His Gly
65                  70                  75                  80

Asn Ala Pro Pro Ala Pro Val Gly Gly Ala Ala Gln Thr His Thr Gln
                85                  90                  95

Pro Pro Val Gln Thr Ala Met Arg Ile Ala Leu Trp Asn Arg Ala Thr
            100                 105                 110

His Gly Glu Gln Gly Ala Leu Gln His Leu Leu Ala Gly Leu Trp Ile
```

```
                115                 120                 125
Gln Thr Glu Ile Ser Pro Asn Ser Gly Asp Ile His Pro Leu Leu Phe
    130                 135                 140

Phe Asp Arg Glu His Ala Glu Ile Thr Phe Ser Arg Ala Ser Val Gln
145                 150                 155                 160

Glu Ile Phe Leu Val Asp Ser Ala His Thr His Arg Lys Thr Val Ser
                165                 170                 175

Phe Leu Thr Arg Asn Thr Ala Ile Ser Ser Ile Arg Arg Leu Glu
            180                 185                 190

Val Thr Phe Glu Ser His Glu Val Ile His Val Arg Ala Val Glu Asp
        195                 200                 205

Val Ala Arg Leu Lys Ile Gly Ser Thr Ser Met Trp Asp Gly Gln Tyr
    210                 215                 220

Thr Arg Tyr His Ala Gly Pro Ala Ser Ala Pro Ser Pro
225                 230                 235
```

<210> SEQ ID NO 3
<211> LENGTH: 213
<212> TYPE: PRT
<213> ORGANISM: Treponema pallidum

<400> SEQUENCE: 3

```
Phe Gln His Gly His Val Pro Pro Arg Arg Ile Pro Pro His Asp Thr
1               5                   10                  15

Phe Gly Ala Leu Pro Thr Ala Ala Leu Pro Ser Asn Ala Arg Asp Thr
            20                  25                  30

Ala Ala His Pro Ser Asp Thr Ala Asp Asn Thr Ser Gly Ser Ser Thr
        35                  40                  45

Thr Thr Asp Pro Arg Ser His Gly Asn Ala Pro Pro Ala Pro Val Gly
    50                  55                  60

Gly Ala Ala Gln Thr His Thr Gln Pro Pro Val Gln Thr Ala Met Arg
65                  70                  75                  80

Ile Ala Leu Trp Asn Arg Ala Thr His Gly Glu Gln Gly Ala Leu Gln
                85                  90                  95

His Leu Leu Ala Gly Leu Trp Ile Gln Thr Glu Ile Ser Pro Asn Ser
            100                 105                 110

Gly Asp Ile His Pro Leu Leu Phe Phe Asp Arg Glu His Ala Glu Ile
        115                 120                 125

Thr Phe Ser Arg Ala Ser Val Gln Glu Ile Phe Leu Val Asp Ser Ala
    130                 135                 140

His Thr His Arg Lys Thr Val Ser Phe Leu Thr Arg Asn Thr Ala Ile
145                 150                 155                 160

Ser Ser Ile Arg Arg Leu Glu Val Thr Phe Glu Ser His Glu Val
                165                 170                 175

Ile His Val Arg Ala Val Glu Asp Val Ala Arg Leu Lys Ile Gly Ser
            180                 185                 190

Thr Ser Met Trp Asp Gly Gln Tyr Thr Arg Tyr His Ala Gly Pro Ala
        195                 200                 205

Ser Ala Pro Ser Pro
    210
```

<210> SEQ ID NO 4
<211> LENGTH: 213
<212> TYPE: PRT
<213> ORGANISM: Artificial Sequence
<220> FEATURE:

<223> OTHER INFORMATION: Fragment of Tp0751 (aa 25-237) with a mutated
       active site (H174A)

<400> SEQUENCE: 4

Phe Gln His Gly His Val Pro Pro Arg Arg Ile Pro Pro His Asp Thr
1               5                   10                  15

Phe Gly Ala Leu Pro Thr Ala Ala Leu Pro Ser Asn Ala Arg Asp Thr
            20                  25                  30

Ala Ala His Pro Ser Asp Thr Ala Asp Asn Thr Ser Gly Ser Ser Thr
        35                  40                  45

Thr Thr Asp Pro Arg Ser His Gly Asn Ala Pro Pro Ala Pro Val Gly
    50                  55                  60

Gly Ala Ala Gln Thr His Thr Gln Pro Pro Val Gln Thr Ala Met Arg
65                  70                  75                  80

Ile Ala Leu Trp Asn Arg Ala Thr His Gly Glu Gln Gly Ala Leu Gln
                85                  90                  95

His Leu Leu Ala Gly Leu Trp Ile Gln Thr Glu Ile Ser Pro Asn Ser
            100                 105                 110

Gly Asp Ile His Pro Leu Leu Phe Phe Asp Arg Glu His Ala Glu Ile
        115                 120                 125

Thr Phe Ser Arg Ala Ser Val Gln Glu Ile Phe Leu Val Asp Ser Ala
    130                 135                 140

His Thr His Arg Lys Thr Val Ser Phe Leu Thr Arg Asn Thr Ala Ile
145                 150                 155                 160

Ser Ser Ile Arg Arg Arg Leu Glu Val Thr Phe Glu Ser Ala Glu Val
                165                 170                 175

Ile His Val Arg Ala Val Glu Asp Val Ala Arg Leu Lys Ile Gly Ser
            180                 185                 190

Thr Ser Met Trp Asp Gly Gln Tyr Thr Arg Tyr His Ala Gly Pro Ala
        195                 200                 205

Ser Ala Pro Ser Pro
    210

<210> SEQ ID NO 5
<211> LENGTH: 213
<212> TYPE: PRT
<213> ORGANISM: Artificial Sequence
<220> FEATURE:
<223> OTHER INFORMATION: Fragment of Tp0751 (aa 25-237) with a mutated
       active site (E175A)

<400> SEQUENCE: 5

Phe Gln His Gly His Val Pro Pro Arg Arg Ile Pro Pro His Asp Thr
1               5                   10                  15

Phe Gly Ala Leu Pro Thr Ala Ala Leu Pro Ser Asn Ala Arg Asp Thr
            20                  25                  30

Ala Ala His Pro Ser Asp Thr Ala Asp Asn Thr Ser Gly Ser Ser Thr
        35                  40                  45

Thr Thr Asp Pro Arg Ser His Gly Asn Ala Pro Pro Ala Pro Val Gly
    50                  55                  60

Gly Ala Ala Gln Thr His Thr Gln Pro Pro Val Gln Thr Ala Met Arg
65                  70                  75                  80

Ile Ala Leu Trp Asn Arg Ala Thr His Gly Glu Gln Gly Ala Leu Gln
                85                  90                  95

His Leu Leu Ala Gly Leu Trp Ile Gln Thr Glu Ile Ser Pro Asn Ser
            100                 105                 110

Gly Asp Ile His Pro Leu Leu Phe Phe Asp Arg Glu His Ala Glu Ile
            115                 120                 125

Thr Phe Ser Arg Ala Ser Val Gln Glu Ile Phe Leu Val Asp Ser Ala
        130                 135                 140

His Thr His Arg Lys Thr Val Ser Phe Leu Thr Arg Asn Thr Ala Ile
145                 150                 155                 160

Ser Ser Ile Arg Arg Arg Leu Glu Val Thr Phe Glu Ser His Ala Val
                165                 170                 175

Ile His Val Arg Ala Val Glu Asp Val Ala Arg Leu Lys Ile Gly Ser
            180                 185                 190

Thr Ser Met Trp Asp Gly Gln Tyr Thr Arg Tyr His Ala Gly Pro Ala
        195                 200                 205

Ser Ala Pro Ser Pro
    210

<210> SEQ ID NO 6
<211> LENGTH: 213
<212> TYPE: PRT
<213> ORGANISM: Artificial Sequence
<220> FEATURE:
<223> OTHER INFORMATION: Fragment of Tp0751 (aa 25-237) with a mutated
      active site (H178A)

<400> SEQUENCE: 6

Phe Gln His Gly His Val Pro Pro Arg Arg Ile Pro Pro His Asp Thr
1               5                   10                  15

Phe Gly Ala Leu Pro Thr Ala Ala Leu Pro Ser Asn Ala Arg Asp Thr
            20                  25                  30

Ala Ala His Pro Ser Asp Thr Ala Asp Asn Thr Ser Gly Ser Ser Thr
        35                  40                  45

Thr Thr Asp Pro Arg Ser His Gly Asn Ala Pro Pro Ala Pro Val Gly
    50                  55                  60

Gly Ala Ala Gln Thr His Thr Gln Pro Pro Val Gln Thr Ala Met Arg
65                  70                  75                  80

Ile Ala Leu Trp Asn Arg Ala Thr His Gly Glu Gln Gly Ala Leu Gln
                85                  90                  95

His Leu Leu Ala Gly Leu Trp Ile Gln Thr Glu Ile Ser Pro Asn Ser
            100                 105                 110

Gly Asp Ile His Pro Leu Leu Phe Phe Asp Arg Glu His Ala Glu Ile
            115                 120                 125

Thr Phe Ser Arg Ala Ser Val Gln Glu Ile Phe Leu Val Asp Ser Ala
        130                 135                 140

His Thr His Arg Lys Thr Val Ser Phe Leu Thr Arg Asn Thr Ala Ile
145                 150                 155                 160

Ser Ser Ile Arg Arg Arg Leu Glu Val Thr Phe Glu Ser His Glu Val
                165                 170                 175

Ile Ala Val Arg Ala Val Glu Asp Val Ala Arg Leu Lys Ile Gly Ser
            180                 185                 190

Thr Ser Met Trp Asp Gly Gln Tyr Thr Arg Tyr His Ala Gly Pro Ala
        195                 200                 205

Ser Ala Pro Ser Pro
    210

<210> SEQ ID NO 7
<211> LENGTH: 214
<212> TYPE: PRT
<213> ORGANISM: Treponema pallidum

<400> SEQUENCE: 7

```
Cys Phe Gln His Gly His Val Pro Pro Arg Ile Pro Pro His Asp
1               5                   10                  15

Thr Phe Gly Ala Leu Pro Thr Ala Ala Leu Pro Ser Asn Ala Arg Asp
            20                  25                  30

Thr Ala Ala His Pro Ser Asp Thr Ala Asp Asn Thr Ser Gly Ser Ser
        35                  40                  45

Thr Thr Thr Asp Pro Arg Ser His Gly Asn Ala Pro Pro Ala Pro Val
    50                  55                  60

Gly Gly Ala Ala Gln Thr His Thr Gln Pro Pro Val Gln Thr Ala Met
65                  70                  75                  80

Arg Ile Ala Leu Trp Asn Arg Ala Thr His Gly Glu Gln Gly Ala Leu
                85                  90                  95

Gln His Leu Leu Ala Gly Leu Trp Ile Gln Thr Glu Ile Ser Pro Asn
            100                 105                 110

Ser Gly Asp Ile His Pro Leu Leu Phe Phe Asp Arg Glu His Ala Glu
        115                 120                 125

Ile Thr Phe Ser Arg Ala Ser Val Gln Glu Ile Phe Leu Val Asp Ser
    130                 135                 140

Ala His Thr His Arg Lys Thr Val Ser Phe Leu Thr Arg Asn Thr Ala
145                 150                 155                 160

Ile Ser Ser Ile Arg Arg Leu Glu Val Thr Phe Glu Ser His Glu
                165                 170                 175

Val Ile His Val Arg Ala Val Glu Asp Val Ala Arg Leu Lys Ile Gly
            180                 185                 190

Ser Thr Ser Met Trp Asp Gly Gln Tyr Thr Arg Tyr His Ala Gly Pro
        195                 200                 205

Ala Ser Ala Pro Ser Pro
        210
```

<210> SEQ ID NO 8
<211> LENGTH: 214
<212> TYPE: PRT
<213> ORGANISM: Artificial Sequence
<220> FEATURE:
<223> OTHER INFORMATION: Fragment of Tp0751 (aa 24-237) with a mutated active site (H175A)

<400> SEQUENCE: 8

```
Cys Phe Gln His Gly His Val Pro Pro Arg Ile Pro Pro His Asp
1               5                   10                  15

Thr Phe Gly Ala Leu Pro Thr Ala Ala Leu Pro Ser Asn Ala Arg Asp
            20                  25                  30

Thr Ala Ala His Pro Ser Asp Thr Ala Asp Asn Thr Ser Gly Ser Ser
        35                  40                  45

Thr Thr Thr Asp Pro Arg Ser His Gly Asn Ala Pro Pro Ala Pro Val
    50                  55                  60

Gly Gly Ala Ala Gln Thr His Thr Gln Pro Pro Val Gln Thr Ala Met
65                  70                  75                  80

Arg Ile Ala Leu Trp Asn Arg Ala Thr His Gly Glu Gln Gly Ala Leu
                85                  90                  95

Gln His Leu Leu Ala Gly Leu Trp Ile Gln Thr Glu Ile Ser Pro Asn
            100                 105                 110

Ser Gly Asp Ile His Pro Leu Leu Phe Phe Asp Arg Glu His Ala Glu
        115                 120                 125
```

Ile Thr Phe Ser Arg Ala Ser Val Gln Glu Ile Phe Leu Val Asp Ser
            130                 135                 140

Ala His Thr His Arg Lys Thr Val Ser Phe Leu Thr Arg Asn Thr Ala
145                 150                 155                 160

Ile Ser Ser Ile Arg Arg Arg Leu Glu Val Thr Phe Glu Ser Ala Glu
                165                 170                 175

Val Ile His Val Arg Ala Val Glu Asp Val Ala Arg Leu Lys Ile Gly
            180                 185                 190

Ser Thr Ser Met Trp Asp Gly Gln Tyr Thr Arg Tyr His Ala Gly Pro
        195                 200                 205

Ala Ser Ala Pro Ser Pro
    210

<210> SEQ ID NO 9
<211> LENGTH: 214
<212> TYPE: PRT
<213> ORGANISM: Artificial Sequence
<220> FEATURE:
<223> OTHER INFORMATION: Fragment of Tp0751 (aa 24-237) with a mutated
      active site (E176A)

<400> SEQUENCE: 9

Cys Phe Gln His Gly His Val Pro Pro Arg Arg Ile Pro Pro His Asp
1               5                   10                  15

Thr Phe Gly Ala Leu Pro Thr Ala Ala Leu Pro Ser Asn Ala Arg Asp
            20                  25                  30

Thr Ala Ala His Pro Ser Asp Thr Ala Asp Asn Thr Ser Gly Ser Ser
        35                  40                  45

Thr Thr Thr Asp Pro Arg Ser His Gly Asn Ala Pro Pro Ala Pro Val
50                  55                  60

Gly Gly Ala Ala Gln Thr His Thr Gln Pro Pro Val Gln Thr Ala Met
65                  70                  75                  80

Arg Ile Ala Leu Trp Asn Arg Ala Thr His Gly Glu Gln Gly Ala Leu
                85                  90                  95

Gln His Leu Leu Ala Gly Leu Trp Ile Gln Thr Glu Ile Ser Pro Asn
            100                 105                 110

Ser Gly Asp Ile His Pro Leu Leu Phe Phe Asp Arg Glu His Ala Glu
        115                 120                 125

Ile Thr Phe Ser Arg Ala Ser Val Gln Glu Ile Phe Leu Val Asp Ser
    130                 135                 140

Ala His Thr His Arg Lys Thr Val Ser Phe Leu Thr Arg Asn Thr Ala
145                 150                 155                 160

Ile Ser Ser Ile Arg Arg Arg Leu Glu Val Thr Phe Glu Ser His Ala
                165                 170                 175

Val Ile His Val Arg Ala Val Glu Asp Val Ala Arg Leu Lys Ile Gly
            180                 185                 190

Ser Thr Ser Met Trp Asp Gly Gln Tyr Thr Arg Tyr His Ala Gly Pro
        195                 200                 205

Ala Ser Ala Pro Ser Pro
    210

<210> SEQ ID NO 10
<211> LENGTH: 214
<212> TYPE: PRT
<213> ORGANISM: Artificial Sequence
<220> FEATURE:
<223> OTHER INFORMATION: Fragment of Tp0751 (aa 24-237) with a mutated active site (H179A)

<400> SEQUENCE: 10

Cys Phe Gln His Gly His Val Pro Pro Arg Ile Pro Pro His Asp
1               5                   10                  15

Thr Phe Gly Ala Leu Pro Thr Ala Leu Pro Ser Asn Ala Arg Asp
            20                  25                  30

Thr Ala Ala His Pro Ser Asp Thr Ala Asp Asn Thr Ser Gly Ser Ser
        35                  40                  45

Thr Thr Thr Asp Pro Arg Ser His Gly Asn Ala Pro Pro Ala Pro Val
50                  55                  60

Gly Gly Ala Ala Gln Thr His Thr Gln Pro Pro Val Gln Thr Ala Met
65                  70                  75                  80

Arg Ile Ala Leu Trp Asn Arg Ala Thr His Gly Glu Gln Gly Ala Leu
                85                  90                  95

Gln His Leu Leu Ala Gly Leu Trp Ile Gln Thr Glu Ile Ser Pro Asn
            100                 105                 110

Ser Gly Asp Ile His Pro Leu Leu Phe Phe Asp Arg Glu His Ala Glu
        115                 120                 125

Ile Thr Phe Ser Arg Ala Ser Val Gln Glu Ile Phe Leu Val Asp Ser
    130                 135                 140

Ala His Thr His Arg Lys Thr Val Ser Phe Leu Thr Arg Asn Thr Ala
145                 150                 155                 160

Ile Ser Ser Ile Arg Arg Arg Leu Glu Val Thr Phe Glu Ser His Glu
                165                 170                 175

Val Ile Ala Val Arg Ala Val Glu Asp Val Ala Arg Leu Lys Ile Gly
            180                 185                 190

Ser Thr Ser Met Trp Asp Gly Gln Tyr Thr Arg Tyr His Ala Gly Pro
        195                 200                 205

Ala Ser Ala Pro Ser Pro
    210

<210> SEQ ID NO 11
<211> LENGTH: 9
<212> TYPE: PRT
<213> ORGANISM: Artificial Sequence
<220> FEATURE:
<223> OTHER INFORMATION: myc-Tag

<400> SEQUENCE: 11

Glu Gln Lys Leu Ile Ser Glu Glu Asp
1               5

<210> SEQ ID NO 12
<211> LENGTH: 8
<212> TYPE: PRT
<213> ORGANISM: Artificial Sequence
<220> FEATURE:
<223> OTHER INFORMATION: FLAG-Tag

<400> SEQUENCE: 12

Asp Tyr Lys Asp Asp Asp Asp Lys
1               5

<210> SEQ ID NO 13
<211> LENGTH: 15
<212> TYPE: PRT
<213> ORGANISM: Artificial Sequence
<220> FEATURE:
<223> OTHER INFORMATION: S-tag -continued

<400> SEQUENCE: 13

Lys Glu Thr Ala Ala Lys Phe Glu Arg Gln His Met Asp Ser
1               5                   10                  15

<210> SEQ ID NO 14
<211> LENGTH: 483
<212> TYPE: DNA
<213> ORGANISM: Artificial Sequence
<220> FEATURE:
<223> OTHER INFORMATION: fragment Tp0751_S78-P237
<220> FEATURE:
<221> NAME/KEY: CDS
<222> LOCATION: (1)..(483)

<400> SEQUENCE: 14

```
tca cat gga aac gcc ccg ccg gcc cct gta ggc gga gca gca cag aca    48
Ser His Gly Asn Ala Pro Pro Ala Pro Val Gly Gly Ala Ala Gln Thr
1               5                   10                  15 cac aca caa ccg cct gta caa aca gca atg cgc ata gcc ctt tgg aac    96
His Thr Gln Pro Pro Val Gln Thr Ala Met Arg Ile Ala Leu Trp Asn
            20                  25                  30 cgt gca aca cat ggt gaa cag gga gca ctc cag cac ctc ttg gca gga   144
Arg Ala Thr His Gly Glu Gln Gly Ala Leu Gln His Leu Leu Ala Gly
        35                  40                  45 ctg tgg ata caa act gaa atc tcc ccg aac tca ggc gat atc cat cct   192
Leu Trp Ile Gln Thr Glu Ile Ser Pro Asn Ser Gly Asp Ile His Pro
    50                  55                  60 ctg ctg ttt ttt gac cga gaa cac gcg gag atc aca ttc tca cgc gca   240
Leu Leu Phe Phe Asp Arg Glu His Ala Glu Ile Thr Phe Ser Arg Ala
65                  70                  75                  80 tca gtc caa gaa atc ttc ctg gta gat agc gcg cac aca cac cgc aag   288
Ser Val Gln Glu Ile Phe Leu Val Asp Ser Ala His Thr His Arg Lys
                85                  90                  95 acg gtg tca ttt ctc acg cgc aac acc gca att tcc agc atc cgc cgc   336
Thr Val Ser Phe Leu Thr Arg Asn Thr Ala Ile Ser Ser Ile Arg Arg
            100                 105                 110 cgc ctt gag gta aca ttt gaa tcc cac gag gtg ata cac gta agg gcg   384
Arg Leu Glu Val Thr Phe Glu Ser His Glu Val Ile His Val Arg Ala
        115                 120                 125 gtt gaa gac gta gca cgg ctc aaa att ggc agc acg tcg atg tgg gac   432
Val Glu Asp Val Ala Arg Leu Lys Ile Gly Ser Thr Ser Met Trp Asp
    130                 135                 140 ggt caa tac acc aga tat cac gcc ggt ccg gct agt gct cct tcg ccc   480
Gly Gln Tyr Thr Arg Tyr His Ala Gly Pro Ala Ser Ala Pro Ser Pro
145                 150                 155                 160 tga                                                               483
```

<210> SEQ ID NO 15
<211> LENGTH: 160
<212> TYPE: PRT
<213> ORGANISM: Artificial Sequence
<220> FEATURE:
<223> OTHER INFORMATION: Synthetic Construct

<400> SEQUENCE: 15

Ser His Gly Asn Ala Pro Pro Ala Pro Val Gly Gly Ala Ala Gln Thr
1               5                   10                  15

His Thr Gln Pro Pro Val Gln Thr Ala Met Arg Ile Ala Leu Trp Asn
            20                  25                  30

Arg Ala Thr His Gly Glu Gln Gly Ala Leu Gln His Leu Leu Ala Gly
        35                  40                  45

Leu Trp Ile Gln Thr Glu Ile Ser Pro Asn Ser Gly Asp Ile His Pro
             50                  55                  60

Leu Leu Phe Phe Asp Arg Glu His Ala Glu Ile Thr Phe Ser Arg Ala
 65                  70                  75                  80

Ser Val Gln Glu Ile Phe Leu Val Asp Ser Ala His Thr His Arg Lys
                 85                  90                  95

Thr Val Ser Phe Leu Thr Arg Asn Thr Ala Ile Ser Ser Ile Arg Arg
            100                 105                 110

Arg Leu Glu Val Thr Phe Glu Ser His Glu Val Ile His Val Arg Ala
        115                 120                 125

Val Glu Asp Val Ala Arg Leu Lys Ile Gly Ser Thr Ser Met Trp Asp
130                 135                 140

Gly Gln Tyr Thr Arg Tyr His Ala Gly Pro Ala Ser Ala Pro Ser Pro
145                 150                 155                 160

<210> SEQ ID NO 16
<211> LENGTH: 160
<212> TYPE: PRT
<213> ORGANISM: Artificial Sequence
<220> FEATURE:
<223> OTHER INFORMATION: Tp0751_S78-P237A

<400> SEQUENCE: 16

Ser His Gly Asn Ala Pro Pro Ala Pro Val Gly Gly Ala Ala Gln Thr
 1               5                  10                  15

His Thr Gln Pro Pro Val Gln Thr Ala Met Arg Ile Ala Leu Trp Asn
             20                  25                  30

Arg Ala Thr His Gly Glu Gln Gly Ala Leu Gln His Leu Leu Ala Gly
         35                  40                  45

Leu Trp Ile Gln Thr Glu Ile Ser Pro Asn Ser Gly Asp Ile His Pro
     50                  55                  60

Leu Leu Phe Phe Asp Arg Glu His Ala Glu Ile Thr Phe Ser Arg Ala
 65                  70                  75                  80

Ser Val Gln Glu Ile Phe Leu Val Asp Ser Ala His Thr His Arg Lys
                 85                  90                  95

Thr Val Ser Phe Leu Thr Arg Asn Thr Ala Ile Ser Ser Ile Arg Arg
            100                 105                 110

Arg Leu Glu Val Thr Phe Glu Ser His Ala Val Ile His Val Arg Ala
        115                 120                 125

Val Glu Asp Val Ala Arg Leu Lys Ile Gly Ser Thr Ser Met Trp Asp
130                 135                 140

Gly Gln Tyr Thr Arg Tyr His Ala Gly Pro Ala Ser Ala Pro Ser Pro
145                 150                 155                 160

<210> SEQ ID NO 17
<211> LENGTH: 420
<212> TYPE: DNA
<213> ORGANISM: Artificial Sequence
<220> FEATURE:
<223> OTHER INFORMATION: fragment Tp0751_V99-P237
<220> FEATURE:
<221> NAME/KEY: CDS
<222> LOCATION: (1)..(420)

<400> SEQUENCE: 17 gta caa aca gca atg cgc ata gcc ctt tgg aac cgt gca aca cat ggt    48
Val Gln Thr Ala Met Arg Ile Ala Leu Trp Asn Arg Ala Thr His Gly
 1               5                  10                  15

| | | | | | | | | | | | | | | |
|---|---|---|---|---|---|---|---|---|---|---|---|---|---|---|
| gaa | cag | gga | gca | ctc | cag | cac | ctc | ttg | gca | gga | ctg | tgg | ata | caa | act | 96 |
| Glu | Gln | Gly | Ala | Leu | Gln | His | Leu | Leu | Ala | Gly | Leu | Trp | Ile | Gln | Thr | |
| | | | 20 | | | | 25 | | | | | 30 | | | | |

| gaa | atc | tcc | ccg | aac | tca | ggc | gat | atc | cat | cct | ctg | ctg | ttt | ttt | gac | 144 |
| Glu | Ile | Ser | Pro | Asn | Ser | Gly | Asp | Ile | His | Pro | Leu | Leu | Phe | Phe | Asp | |
| | 35 | | | | | 40 | | | | | 45 | | | | | |

| cga | gaa | cac | gcg | gag | atc | aca | ttc | tca | cgc | gca | tca | gtc | caa | gaa | atc | 192 |
| Arg | Glu | His | Ala | Glu | Ile | Thr | Phe | Ser | Arg | Ala | Ser | Val | Gln | Glu | Ile | |
| 50 | | | | | 55 | | | | | 60 | | | | | | |

| ttc | ctg | gta | gat | agc | gcg | cac | aca | cac | cgc | aag | acg | gtg | tca | ttt | ctc | 240 |
| Phe | Leu | Val | Asp | Ser | Ala | His | Thr | His | Arg | Lys | Thr | Val | Ser | Phe | Leu | |
| 65 | | | | | 70 | | | | | 75 | | | | | 80 | |

| acg | cgc | aac | acc | gca | att | tcc | agc | atc | cgc | cgc | ctt | gag | gta | aca | | 288 |
| Thr | Arg | Asn | Thr | Ala | Ile | Ser | Ser | Ile | Arg | Arg | Leu | Glu | Val | Thr | | |
| | | | | 85 | | | | | 90 | | | | | 95 | | |

| ttt | gaa | tcc | cac | gag | gtg | ata | cac | gta | agg | gcg | gtt | gaa | gac | gta | gca | 336 |
| Phe | Glu | Ser | His | Glu | Val | Ile | His | Val | Arg | Ala | Val | Glu | Asp | Val | Ala | |
| | | | | 100 | | | | | 105 | | | | | 110 | | |

| cgg | ctc | aaa | att | ggc | agc | acg | tcg | atg | tgg | gac | ggt | caa | tac | acc | aga | 384 |
| Arg | Leu | Lys | Ile | Gly | Ser | Thr | Ser | Met | Trp | Asp | Gly | Gln | Tyr | Thr | Arg | |
| | | | 115 | | | | | 120 | | | | | 125 | | | |

| tat | cac | gcc | ggt | ccg | gct | agt | gct | cct | tcg | ccc | tga | | | | | 420 |
| Tyr | His | Ala | Gly | Pro | Ala | Ser | Ala | Pro | Ser | Pro | | | | | | |
| | 130 | | | | | 135 | | | | | | | | | | |

<210> SEQ ID NO 18
<211> LENGTH: 139
<212> TYPE: PRT
<213> ORGANISM: Artificial Sequence
<220> FEATURE:
<223> OTHER INFORMATION: Synthetic Construct

<400> SEQUENCE: 18

Val Gln Thr Ala Met Arg Ile Ala Leu Trp Asn Arg Ala Thr His Gly
1               5                   10                  15

Glu Gln Gly Ala Leu Gln His Leu Leu Ala Gly Leu Trp Ile Gln Thr
            20                  25                  30

Glu Ile Ser Pro Asn Ser Gly Asp Ile His Pro Leu Leu Phe Phe Asp
        35                  40                  45

Arg Glu His Ala Glu Ile Thr Phe Ser Arg Ala Ser Val Gln Glu Ile
    50                  55                  60

Phe Leu Val Asp Ser Ala His Thr His Arg Lys Thr Val Ser Phe Leu
65                  70                  75                  80

Thr Arg Asn Thr Ala Ile Ser Ser Ile Arg Arg Leu Glu Val Thr
                85                  90                  95

Phe Glu Ser His Glu Val Ile His Val Arg Ala Val Glu Asp Val Ala
                100                 105                 110

Arg Leu Lys Ile Gly Ser Thr Ser Met Trp Asp Gly Gln Tyr Thr Arg
            115                 120                 125

Tyr His Ala Gly Pro Ala Ser Ala Pro Ser Pro
        130                 135

<210> SEQ ID NO 19
<211> LENGTH: 139
<212> TYPE: PRT
<213> ORGANISM: Artificial Sequence
<220> FEATURE:
<223> OTHER INFORMATION: Tp0751_V99-P273A

<400> SEQUENCE: 19

```
Val Gln Thr Ala Met Arg Ile Ala Leu Trp Asn Arg Ala Thr His Gly
1               5                   10                  15

Glu Gln Gly Ala Leu Gln His Leu Leu Ala Gly Leu Trp Ile Gln Thr
            20                  25                  30

Glu Ile Ser Pro Asn Ser Gly Asp Ile His Pro Leu Leu Phe Phe Asp
        35                  40                  45

Arg Glu His Ala Glu Ile Thr Phe Ser Arg Ala Ser Val Gln Glu Ile
    50                  55                  60

Phe Leu Val Asp Ser Ala His Thr His Arg Lys Thr Val Ser Phe Leu
65                  70                  75                  80

Thr Arg Asn Thr Ala Ile Ser Ser Ile Arg Arg Arg Leu Glu Val Thr
                85                  90                  95

Phe Glu Ser His Ala Val Ile His Val Arg Ala Val Glu Asp Val Ala
            100                 105                 110

Arg Leu Lys Ile Gly Ser Thr Ser Met Trp Asp Gly Gln Tyr Thr Arg
        115                 120                 125

Tyr His Ala Gly Pro Ala Ser Ala Pro Ser Pro
    130                 135

<210> SEQ ID NO 20
<211> LENGTH: 372
<212> TYPE: DNA
<213> ORGANISM: Artificial Sequence
<220> FEATURE:
<223> OTHER INFORMATION: fragment Tp0751_E115-P237
<220> FEATURE:
<221> NAME/KEY: CDS
<222> LOCATION: (1)..(372)

<400> SEQUENCE: 20 gaa cag gga gca ctc cag cac ctc ttg gca gga ctg tgg ata caa act     48
Glu Gln Gly Ala Leu Gln His Leu Leu Ala Gly Leu Trp Ile Gln Thr
1               5                   10                  15 gaa atc tcc ccg aac tca ggc gat atc cat cct ctg ctg ttt ttt gac     96
Glu Ile Ser Pro Asn Ser Gly Asp Ile His Pro Leu Leu Phe Phe Asp
            20                  25                  30 cga gaa cac gcg gag atc aca ttc tca cgc gca tca gtc caa gaa atc    144
Arg Glu His Ala Glu Ile Thr Phe Ser Arg Ala Ser Val Gln Glu Ile
        35                  40                  45 ttc ctg gta gat agc gcg cac aca cac cgc aag acg gtg tca ttt ctc    192
Phe Leu Val Asp Ser Ala His Thr His Arg Lys Thr Val Ser Phe Leu
    50                  55                  60 acg cgc aac acc gca att tcc agc atc cgc cgc cgc ctt gag gta aca    240
Thr Arg Asn Thr Ala Ile Ser Ser Ile Arg Arg Arg Leu Glu Val Thr
65                  70                  75                  80 ttt gaa tcc cac gag gtg ata cac gta agg gcg gtt gaa gac gta gca    288
Phe Glu Ser His Glu Val Ile His Val Arg Ala Val Glu Asp Val Ala
                85                  90                  95 cgg ctc aaa att ggc agc acg tcg atg tgg gac ggt caa tac acc aga    336
Arg Leu Lys Ile Gly Ser Thr Ser Met Trp Asp Gly Gln Tyr Thr Arg
            100                 105                 110 tat cac gcc ggt ccg gct agt gct cct tcg ccc tga                    372
Tyr His Ala Gly Pro Ala Ser Ala Pro Ser Pro
        115                 120

<210> SEQ ID NO 21
<211> LENGTH: 123
<212> TYPE: PRT
<213> ORGANISM: Artificial Sequence
<220> FEATURE:
<223> OTHER INFORMATION: Synthetic Construct
```

<400> SEQUENCE: 21

Glu Gln Gly Ala Leu Gln His Leu Leu Ala Gly Leu Trp Ile Gln Thr
1               5                   10                  15

Glu Ile Ser Pro Asn Ser Gly Asp Ile His Pro Leu Leu Phe Phe Asp
            20                  25                  30

Arg Glu His Ala Glu Ile Thr Phe Ser Arg Ala Ser Val Gln Glu Ile
        35                  40                  45

Phe Leu Val Asp Ser Ala His Thr His Arg Lys Thr Val Ser Phe Leu
    50                  55                  60

Thr Arg Asn Thr Ala Ile Ser Ser Ile Arg Arg Leu Glu Val Thr
65                  70                  75                  80

Phe Glu Ser His Glu Val Ile His Val Arg Ala Val Glu Asp Val Ala
                85                  90                  95

Arg Leu Lys Ile Gly Ser Thr Ser Met Trp Asp Gly Gln Tyr Thr Arg
            100                 105                 110

Tyr His Ala Gly Pro Ala Ser Ala Pro Ser Pro
        115                 120

<210> SEQ ID NO 22
<211> LENGTH: 24
<212> TYPE: PRT
<213> ORGANISM: Artificial Sequence
<220> FEATURE:
<223> OTHER INFORMATION: p1 fragment of Tp0751

<400> SEQUENCE: 22

Thr Ala Ala Leu Pro Ser Asn Ala Arg Asp Thr Ala Ala His Pro Ser
1               5                   10                  15

Asp Thr Ala Asp Asn Thr Ser Gly
            20

<210> SEQ ID NO 23
<211> LENGTH: 24
<212> TYPE: PRT
<213> ORGANISM: Artificial Sequence
<220> FEATURE:
<223> OTHER INFORMATION: p2 fragment of Tp0751

<400> SEQUENCE: 23

Pro Ser Asp Thr Ala Asp Asn Thr Ser Gly Ser Ser Thr Thr Thr Asp
1               5                   10                  15

Pro Arg Ser His Gly Asn Ala Pro
            20

<210> SEQ ID NO 24
<211> LENGTH: 24
<212> TYPE: PRT
<213> ORGANISM: Artificial Sequence
<220> FEATURE:
<223> OTHER INFORMATION: p3 fragment of Tp0751

<400> SEQUENCE: 24

Thr Asp Pro Arg Ser His Gly Asn Ala Pro Ala Pro Val Gly Gly
1               5                   10                  15

Ala Ala Gln Thr His Thr Gln Pro
            20

<210> SEQ ID NO 25
<211> LENGTH: 24
<212> TYPE: PRT

```
<213> ORGANISM: Artificial Sequence
<220> FEATURE:
<223> OTHER INFORMATION: p4 fragment of Tp0751

<400> SEQUENCE: 25

Gly Gly Ala Ala Gln Thr His Thr Gln Pro Pro Val Gln Thr Ala Met
1               5                   10                  15

Arg Ile Ala Leu Trp Asn Arg Ala
            20

<210> SEQ ID NO 26
<211> LENGTH: 24
<212> TYPE: PRT
<213> ORGANISM: Artificial Sequence
<220> FEATURE:
<223> OTHER INFORMATION: p5 fragment of Tp0751

<400> SEQUENCE: 26

Ala Met Arg Ile Ala Leu Trp Asn Arg Ala Thr His Gly Glu Gln Gly
1               5                   10                  15

Ala Leu Gln His Leu Leu Ala Gly
            20

<210> SEQ ID NO 27
<211> LENGTH: 24
<212> TYPE: PRT
<213> ORGANISM: Artificial Sequence
<220> FEATURE:
<223> OTHER INFORMATION: p6 fragment of Tp0751

<400> SEQUENCE: 27

Gln Gly Ala Leu Gln His Leu Leu Ala Gly Leu Trp Ile Gln Thr Glu
1               5                   10                  15

Ile Ser Pro Asn Ser Gly Asp Ile
            20

<210> SEQ ID NO 28
<211> LENGTH: 24
<212> TYPE: PRT
<213> ORGANISM: Artificial Sequence
<220> FEATURE:
<223> OTHER INFORMATION: p7 fragment of Tp0751

<400> SEQUENCE: 28

Thr Glu Ile Ser Pro Asn Ser Gly Asp Ile His Pro Leu Leu Phe Phe
1               5                   10                  15

Asp Arg Glu His Ala Glu Ile Thr
            20

<210> SEQ ID NO 29
<211> LENGTH: 24
<212> TYPE: PRT
<213> ORGANISM: Artificial Sequence
<220> FEATURE:
<223> OTHER INFORMATION: p8 fragment of Tp0751

<400> SEQUENCE: 29

Phe Phe Asp Arg Glu His Ala Glu Ile Thr Phe Ser Arg Ala Ser Val
1               5                   10                  15

Gln Glu Ile Phe Leu Val Asp Ser
            20

<210> SEQ ID NO 30
<211> LENGTH: 24
```

<212> TYPE: PRT
<213> ORGANISM: Artificial Sequence
<220> FEATURE:
<223> OTHER INFORMATION: p9 fragment of Tp0751

<400> SEQUENCE: 30

Ser Val Gln Glu Ile Phe Leu Val Asp Ser Ala His Thr His Arg Lys
1               5                   10                  15

Thr Val Ser Phe Leu Thr Arg Asn
            20

<210> SEQ ID NO 31
<211> LENGTH: 24
<212> TYPE: PRT
<213> ORGANISM: Artificial Sequence
<220> FEATURE:
<223> OTHER INFORMATION: p10 fragment of Tp0751

<400> SEQUENCE: 31

Arg Lys Thr Val Ser Phe Leu Thr Arg Asn Thr Ala Ile Ser Ser Ile
1               5                   10                  15

Arg Arg Arg Leu Glu Val Thr Phe
            20

<210> SEQ ID NO 32
<211> LENGTH: 24
<212> TYPE: PRT
<213> ORGANISM: Artificial Sequence
<220> FEATURE:
<223> OTHER INFORMATION: p11 fragment of Tp0751

<400> SEQUENCE: 32

Ser Ile Arg Arg Arg Leu Glu Val Thr Phe Glu Ser His Glu Val Ile
1               5                   10                  15

His Val Arg Ala Val Glu Asp Val
            20

<210> SEQ ID NO 33
<211> LENGTH: 24
<212> TYPE: PRT
<213> ORGANISM: Artificial Sequence
<220> FEATURE:
<223> OTHER INFORMATION: p12 fragment of Tp0751

<400> SEQUENCE: 33

Val Ile His Val Arg Ala Val Glu Asp Val Ala Arg Leu Lys Ile Gly
1               5                   10                  15

Ser Thr Ser Met Trp Asp Gly Gln
            20

<210> SEQ ID NO 34
<211> LENGTH: 24
<212> TYPE: PRT
<213> ORGANISM: Artificial Sequence
<220> FEATURE:
<223> OTHER INFORMATION: p13 fragment of Tp0751

<400> SEQUENCE: 34

Ile Gly Ser Thr Ser Met Trp Asp Gly Gln Tyr Thr Arg Tyr His Ala
1               5                   10                  15

Gly Pro Ala Ser Ala Pro Ser Pro
            20

<210> SEQ ID NO 35

```
<211> LENGTH: 24
<212> TYPE: PRT
<213> ORGANISM: Artificial Sequence
<220> FEATURE:
<223> OTHER INFORMATION: p4scr

<400> SEQUENCE: 35

Met Arg Leu Thr Pro Gly Trp His Thr Ala Asn Gln Ile Arg Pro Gln
1               5                   10                  15

Ala Gln Gly Val Ala Thr Ala Ala
            20

<210> SEQ ID NO 36
<211> LENGTH: 24
<212> TYPE: PRT
<213> ORGANISM: Artificial Sequence
<220> FEATURE:
<223> OTHER INFORMATION: p6scr

<400> SEQUENCE: 36

Thr Ser Asn Asp Trp Gly Gln Ser Leu Ala Ile Leu His Glu Pro Gln
1               5                   10                  15

Leu Gly Ile Leu Gln Ala Gly Ile
            20

<210> SEQ ID NO 37
<211> LENGTH: 24
<212> TYPE: PRT
<213> ORGANISM: Artificial Sequence
<220> FEATURE:
<223> OTHER INFORMATION: p10scr

<400> SEQUENCE: 37

Thr Ser Arg Val Lys Leu Thr Ile Ser Phe Glu Arg Ser Leu Val Asn
1               5                   10                  15

Arg Thr Arg Thr Ala Arg Phe Ile
            20

<210> SEQ ID NO 38
<211> LENGTH: 13
<212> TYPE: PRT
<213> ORGANISM: Artificial Sequence
<220> FEATURE:
<223> OTHER INFORMATION: portion of nitrophorin 4

<400> SEQUENCE: 38

Phe Asn Gly Asp Val Trp Tyr Val Leu Asn Arg Asn Lys
1               5                   10

<210> SEQ ID NO 39
<211> LENGTH: 12
<212> TYPE: PRT
<213> ORGANISM: Artificial Sequence
<220> FEATURE:
<223> OTHER INFORMATION: portion of triabin

<400> SEQUENCE: 39

Phe Asn Gly Thr Trp Tyr Leu Phe Glu Arg Thr Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: portion of metalloproteinase inhibitor
```

```
<400> SEQUENCE: 40

Leu Ser Gly Gln Trp Val Leu Lys Lys Lys Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: portion of hNGAL

<400> SEQUENCE: 41

Phe Gln Gly Lys Trp Tyr Val Tyr Gly Arg Thr Lys
1               5                   10

<210> SEQ ID NO 42
<211> LENGTH: 4
<212> TYPE: PRT
<213> ORGANISM: Artificial Sequence
<220> FEATURE:
<223> OTHER INFORMATION: binding motif
<220> FEATURE:
<221> NAME/KEY: MISC_FEATURE
<222> LOCATION: (3)..(3)
<223> OTHER INFORMATION: X iis any amino acid
<220> FEATURE:
<221> NAME/KEY: MISC_FEATURE
<222> LOCATION: (4)..(4)
<223> OTHER INFORMATION: X iis R or K

<400> SEQUENCE: 42

Arg Arg Xaa Xaa
1

<210> SEQ ID NO 43
<211> LENGTH: 5
<212> TYPE: PRT
<213> ORGANISM: Artificial Sequence
<220> FEATURE:
<223> OTHER INFORMATION: binding motif
<220> FEATURE:
<221> NAME/KEY: MISC_FEATURE
<222> LOCATION: (1)..(2)
<223> OTHER INFORMATION: X is any amino acid
<220> FEATURE:
<221> NAME/KEY: MISC_FEATURE
<222> LOCATION: (3)..(3)
<223> OTHER INFORMATION: X is R or K
<220> FEATURE:
<221> NAME/KEY: MISC_FEATURE
<222> LOCATION: (4)..(5)
<223> OTHER INFORMATION: X is any amino acid

<400> SEQUENCE: 43

Xaa Xaa Xaa Xaa Xaa
1               5

<210> SEQ ID NO 44
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(5)
```

```
<223> OTHER INFORMATION: X is any amino acid

<400> SEQUENCE: 44

Arg Xaa Arg Xaa Xaa Arg
1               5

<210> SEQ ID NO 45
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: Xaa
<222> LOCATION: (3)..(4)
<223> OTHER INFORMATION: Xaa is a mutated amino acid.
<220> FEATURE:
<221> NAME/KEY: Xaa
<222> LOCATION: (3)..(4)
<223> OTHER INFORMATION: X is any amino acid.

<400> SEQUENCE: 45

His Glu Xaa Xaa His
1               5
```